(12) United States Patent
Mukhtar et al.

(10) Patent No.: US 8,759,586 B2
(45) Date of Patent: Jun. 24, 2014

(54) PROCESSES FOR THE PREPARATION OF CINACALCET

(75) Inventors: Sayeed Mukhtar, West Singhbhum (IN); Dinesh Shashidharan Nair, Vadodara (IN); Roshan Ramesh Medhane, Nashik (IN); Nitin Maheshwari, New Delhi (IN); Hashim Nizar Poovanathil Nagoor Meeran, Pathanamthitta (IN); Neera Tewari, Gurgaon (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 81 days.

(21) Appl. No.: 13/496,834

(22) PCT Filed: Sep. 16, 2010

(86) PCT No.: PCT/IB2010/054197
§ 371 (c)(1),
(2), (4) Date: Jul. 25, 2012

(87) PCT Pub. No.: WO2011/033473
PCT Pub. Date: Mar. 24, 2011

(65) Prior Publication Data
US 2012/0309842 A1  Dec. 6, 2012

(30) Foreign Application Priority Data

Sep. 16, 2009 (IN) ............................. 1937/DEL/2009
Dec. 31, 2009 (IN) ............................. 2749/DEL/2009
Jan. 29, 2010 (IN) ............................... 195/DEL/2010
Jan. 29, 2010 (IN) ............................... 199/DEL/2010
Jun. 25, 2010 (IN) ............................. 1494/DEL/2010

(51) Int. Cl.
*C07C 211/00* (2006.01)

(52) U.S. Cl.
USPC .......................................................... 564/336

(58) Field of Classification Search
USPC ......................................................... 564/336
See application file for complete search history.

(56) References Cited

U.S. PATENT DOCUMENTS

| | | | |
|---|---|---|---|
| 6,011,068 A | 1/2000 | Nemeth et al. | 514/654 |
| 6,031,003 A | 2/2000 | Nemeth et al. | 514/579 |
| 6,211,244 B1 | 4/2001 | Van Wagenen et al. | 514/649 |
| 6,313,146 B1 | 11/2001 | Van Wagenen et al. | 514/337 |
| 7,393,967 B2 | 7/2008 | Lifshitz-Liron | 560/41 |
| 7,563,930 B2 | 7/2009 | Wizel et al. | 564/337 |
| 2007/0238790 A1 | 10/2007 | Liu et al. | 514/649 |
| 2009/0137837 A1 | 5/2009 | Thiel et al. | 560/115 |

FOREIGN PATENT DOCUMENTS

| | | | | |
|---|---|---|---|---|
| WO | WO 2008/019690 | 2/2008 | | A61K 31/137 |
| WO | WO 2008/068625 | 6/2008 | | C07C 209/28 |
| WO | WO 2009/002427 | 12/2008 | | C07C 209/70 |
| WO | WO 2009/153814 | 12/2009 | | C07C 209/28 |
| WO | WO 2010/015935 | 2/2010 | | C07C 211/30 |
| WO | WO 2010/094674 | 8/2010 | | C07C 209/68 |

OTHER PUBLICATIONS

Sorbera et al., "Cinacalcet Hydrochloride. *Treatment of Hyperparathyroidism*", *Drugs of the Future*, 27(9):831-836 (2002).

*Primary Examiner* — Wu-Cheng Winston Shen
*Assistant Examiner* — Christopher R Stone

(57) ABSTRACT

The present invention provides processes and intermediates for preparing cinacalcet base and pharmaceutically acceptable salts thereof.

4 Claims, 14 Drawing Sheets

Figure 11
Table 1: Peak table for Figure 1 (Hydrochloride salt of N-[(1R)-1-(naphthalen-1-yl)ethyl]-3-[3-(trifluomethyl)phenyl]prop-2-en-1-amine)

| 2θ position [°] | d-spacing [Å] | Rel. Int [%] |
|---|---|---|
| 6.97 | 12.69 | 55.68 |
| 13.90 | 6.37 | 100.00 |
| 14.20 | 6.24 | 3.68 |
| 14.98 | 5.92 | 10.57 |
| 15.88 | 5.58 | 32.98 |
| 16.16 | 5.49 | 56.73 |
| 17.92 | 4.95 | 2.24 |
| 18.62 | 4.77 | 30.27 |
| 19.01 | 4.67 | 94.10 |
| 20.08 | 4.42 | 20.93 |
| 20.89 | 4.25 | 54.52 |
| 22.37 | 3.97 | 8.50 |
| 22.71 | 3.92 | 12.70 |
| 23.43 | 3.80 | 7.18 |
| 24.27 | 3.67 | 58.80 |
| 25.07 | 3.55 | 3.97 |
| 25.51 | 3.49 | 22.83 |
| 26.40 | 3.38 | 19.72 |
| 26.95 | 3.30 | 11.44 |
| 27.91 | 3.20 | 5.84 |
| 28.46 | 3.14 | 16.88 |
| 28.88 | 3.09 | 3.81 |
| 29.84 | 2.99 | 3.43 |
| 30.63 | 2.92 | 3.38 |
| 31.57 | 2.83 | 18.02 |
| 32.45 | 2.76 | 5.46 |
| 33.91 | 2.64 | 4.26 |
| 34.84 | 2.58 | 7.82 |
| 38.30 | 2.35 | 4.15 |

Figure 12
Table 2: Peak table for Figure 4 (Hydrobromide salt of N-[(1R)-1-(naphthalen-1-yl)ethyl]-3-[3-(trifluomethyl)phenyl]prop-2-en-1-amine)

| 2θ position [°] | d-spacing [Å] | Rel. Int [%] |
|---|---|---|
| 4.52 | 19.54 | 0.87 |
| 6.58 | 13.43 | 4.14 |
| 7.63 | 11.58 | 8.33 |
| 8.30 | 10.65 | 7.47 |
| 9.02 | 9.80 | 13.18 |
| 10.67 | 8.29 | 8.62 |
| 12.31 | 7.19 | 2.43 |
| 13.12 | 6.74 | 43.74 |
| 13.52 | 6.55 | 6.75 |
| 13.79 | 6.42 | 3.37 |
| 14.28 | 6.20 | 95.76 |
| 14.50 | 6.11 | 8.97 |
| 15.26 | 5.80 | 14.60 |
| 15.58 | 5.70 | 6.40 |
| 16.61 | 5.33 | 100.00 |
| 17.45 | 5.09 | 7.99 |
| 18.00 | 4.92 | 3.78 |
| 18.31 | 4.84 | 5.96 |
| 18.49 | 4.80 | 6.74 |
| 18.65 | 4.76 | 5.32 |
| 19.10 | 4.65 | 9.67 |
| 19.37 | 4.58 | 6.50 |
| 19.74 | 4.50 | 72.18 |
| 20.65 | 4.30 | 75.77 |
| 20.96 | 4.24 | 7.68 |
| 21.38 | 4.15 | 15.30 |
| 21.92 | 4.05 | 18.25 |
| 22.46 | 3.96 | 40.70 |
| 22.61 | 3.93 | 19.89 |
| 22.86 | 3.89 | 15.69 |
| 22.96 | 3.87 | 17.18 |
| 23.31 | 3.81 | 11.26 |
| 23.66 | 3.76 | 9.62 |
| 24.12 | 3.69 | 8.72 |
| 24.31 | 3.66 | 12.93 |
| 24.75 | 3.60 | 5.32 |
| 25.26 | 3.52 | 15.39 |
| 25.40 | 3.51 | 17.51 |
| 25.71 | 3.46 | 7.27 |
| 26.03 | 3.42 | 6.08 |
| 26.38 | 3.38 | 20.50 |
| 26.77 | 3.33 | 6.31 |
| 27.20 | 3.28 | 31.13 |
| 27.41 | 3.25 | 7.99 |
| 28.07 | 3.18 | 4.71 |
| 28.58 | 3.12 | 12.13 |
| 28.80 | 3.10 | 11.39 |
| 29.17 | 3.06 | 7.07 |
| 29.60 | 3.01 | 14.47 |
| 30.40 | 2.94 | 4.94 |
| 30.87 | 2.90 | 11.14 |
| 31.54 | 2.83 | 5.20 |
| 31.88 | 2.81 | 4.58 |
| 33.15 | 2.70 | 6.77 |
| 33.90 | 2.64 | 5.29 |
| 35.23 | 2.55 | 6.71 |
| 35.60 | 2.52 | 7.44 |
| 36.52 | 2.46 | 3.99 |
| 37.12 | 2.42 | 3.72 |
| 38.33 | 2.35 | 4.73 |
| 39.38 | 2.29 | 3.87 |

Figure 13
Table 3: Peak table for Figure 5 (Fumarate salt of N-[(1R)-1-(naphthalen-1-yl)ethyl]-3-[3-(trifluomethyl)phenyl]prop-2-en-1-amine)

| 2θ position [°] | d-spacing [Å] | Rel. Int [%] |
|---|---|---|
| 5.38 | 16.43 | 2.39 |
| 8.04 | 11.00 | 100.00 |
| 9.72 | 9.10 | 1.47 |
| 10.73 | 8.24 | 13.44 |
| 11.82 | 7.49 | 14.20 |
| 12.30 | 7.20 | 5.31 |
| 13.43 | 6.60 | 6.57 |
| 14.10 | 6.28 | 16.66 |
| 14.52 | 6.10 | 13.79 |
| 16.03 | 5.53 | 82.67 |
| 16.53 | 5.36 | 24.53 |
| 17.08 | 5.19 | 6.72 |
| 17.62 | 5.03 | 8.31 |
| 18.81 | 4.72 | 99.45 |
| 19.04 | 4.66 | 30.86 |
| 19.56 | 4.54 | 16.98 |
| 21.06 | 4.22 | 61.32 |
| 21.61 | 4.11 | 32.87 |
| 22.24 | 4.00 | 39.80 |
| 22.77 | 3.91 | 17.99 |
| 23.02 | 3.86 | 19.41 |
| 23.59 | 3.77 | 27.41 |
| 24.20 | 3.68 | 27.04 |
| 25.49 | 3.50 | 26.07 |
| 26.32 | 3.39 | 22.58 |
| 27.01 | 3.30 | 23.67 |
| 28.74 | 3.11 | 54.54 |
| 29.80 | 3.00 | 25.37 |
| 31.66 | 2.83 | 88.50 |
| 32.40 | 2.76 | 11.26 |
| 33.27 | 2.69 | 10.60 |
| 35.32 | 2.54 | 6.80 |
| 38.00 | 2.36 | 4.30 |

Figure 14
Table 4: Peak table for Figure 8 (Citrate salt of N-[(1R)-1-(naphthalen-1-yl)ethyl]-3-[3-(trifluomethyl)phenyl]prop-2-en-1-amine)

| 2θ position [°] | d-spacing [Å] | Rel. Int [%] |
|---|---|---|
| 3.73 | 23.68 | 100.00 |
| 7.46 | 11.86 | 2.62 |
| 11.18 | 7.91 | 27.04 |
| 11.82 | 7.49 | 12.57 |
| 12.04 | 7.35 | 20.12 |
| 12.77 | 6.93 | 8.08 |
| 13.34 | 6.64 | 14.94 |
| 13.78 | 6.42 | 7.07 |
| 14.56 | 6.08 | 20.94 |
| 15.66 | 5.66 | 10.64 |
| 16.28 | 5.45 | 15.42 |
| 16.57 | 5.35 | 33.83 |
| 17.31 | 5.12 | 53.38 |
| 17.67 | 5.02 | 62.28 |
| 18.13 | 4.89 | 23.14 |
| 18.34 | 4.84 | 18.80 |
| 18.74 | 4.74 | 16.74 |
| 19.10 | 4.65 | 28.44 |
| 20.13 | 4.41 | 6.97 |
| 21.36 | 4.16 | 40.60 |
| 21.75 | 4.09 | 14.48 |
| 22.76 | 3.91 | 67.98 |
| 23.03 | 3.86 | 28.36 |
| 23.72 | 3.75 | 10.99 |
| 23.91 | 3.72 | 10.65 |
| 24.90 | 3.58 | 27.58 |
| 25.08 | 3.55 | 28.61 |
| 25.59 | 3.48 | 40.72 |
| 25.76 | 3.46 | 43.71 |
| 26.50 | 3.64 | 23.92 |
| 26.89 | 3.32 | 22.39 |
| 28.09 | 3.18 | 10.40 |
| 29.12 | 3.07 | 6.78 |
| 31.61 | 2.83 | 11.34 |
| 32.62 | 2.75 | 5.15 |
| 33.35 | 2.69 | 6.26 |
| 34.46 | 2.60 | 11.51 |
| 36.71 | 2.45 | 12.30 |
| 37.15 | 2.42 | 12.74 |
| 37.94 | 2.37 | 9.70 |
| 38.80 | 2.32 | 9.70 |

PROCESSES FOR THE PREPARATION OF CINACALCET

FIELD OF THE INVENTION

The present invention provides processes and intermediates for preparing cinacalcet base and pharmaceutically acceptable salts thereof.

BACKGROUND OF THE INVENTION

Cinacalcet, chemically designated as N-[1-(R)-(–)-(1-naphthyl)ethyl]-3-[3-(trifluoromethyl)phenyl]-1-aminopropane hydrochloride is a calcimimetic agent that increases the sensitivity of the calcium-sensing receptor to activation by extracellular calcium. It is disclosed in following patents U.S. Pat. Nos. 6,211,244; 6,011,068; 6,313,146 and 6,031,003.

Sensipar® (cinacalcet) is indicated for the treatment of secondary hyperparathyroidism in patients with chronic kidney disease on dialysis and for the treatment of hypercalcemia in patients with parathyroid carcinoma.

U.S. Pat. Nos. 6,011,068; 6,211,244 and 6,313,146 describe cinacalcet base and its pharmaceutically acceptable salts but do not provide any example for its preparation.

Several processes have been reported for the preparation of the cinacalcet base, its derivatives and pharmaceutically acceptable salts thereof.

Drugs (2002), 27(9), 831-836 discloses a synthetic scheme for preparing cinacalcet which is also disclosed as a general procedure in U.S. Pat. No. 6,211,244. The process involves reaction of 3-[3-(trifluoromethyl)phenyl]propionaldehyde prepared by Swern oxidation of the corresponding alcohol with (R)-1-(1-naphthyl)ethylamine in the presence of titanium isopropoxide to give imine which upon reduction gives cinacalcet base. However, the use of highly inflammable and toxic titanium isopropoxide in this process limits its practicability on the industrial scale.

In accordance with U.S. Pat. No. 6,211,244, cinacalcet may also be prepared by reacting 1-acetylnaphthalene with 3-3-[-(trifluoromethyl)phenyl]propylamine in the presence of titanium isopropoxide, followed by reduction using sodium cyanoborohydride and resolution of the resulting recemic cinacalcet base by chiral liquid chromatography. U.S. Pat. No. 6,211,244 also discloses reaction of 3-trichlorocinnamoylnitrile and (R)-1-naphthylethylamine in the presence of diisobutylaluminium hydride (DIBAL) followed by the reduction of the imine intermediate to produce cinacalcet. Diisobutylaluminium hydride is inflammable and not ideal for the commercial scale up.

The process outlined in U.S. Pat. No. 7,393,967 involves combining 1-bromo-3-(trifluoromethyl)benzene with N-[(1R)-1-(naphthalen-1-yl)ethyl]prop-2-en-1-amine in the presence of a catalyst and a base. However, the reaction is carried at a high temperature for about 3 to 24 hours.

The subsequent U.S. Application Publication No. 2009/0137837 describes the process for the preparation of cinacalcet involving allylic amination of 1-[3-(3-trifluoromethyl)phenyl]propene with (R)-1-naphthylethylamine in the presence of transition metal catalyst followed by the reduction. This process involves the use of expensive palladium and platinum catalyst for the condensation and column chromatography for the isolation of intermediates.

Thus there is a need in the art for an improved process for the preparation of cinacalcet which employs less expensive, easily available and environment friendly reagents.

SUMMARY OF THE INVENTION

The present invention provides processes and intermediates for preparing cinacalcet base of Formula I and pharmaceutically acceptable salts thereof, employing non-expensive, easily available reagents.

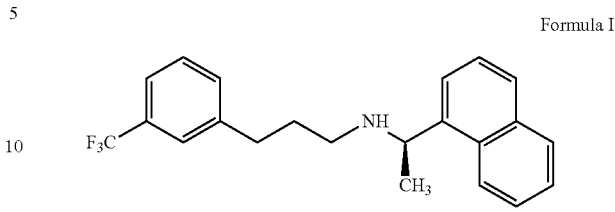

Formula I

The first aspect of the present invention provides a process for preparing cinacalcet base of Formula I and pharmaceutically acceptable salts thereof. The process comprises the steps of a) reacting 1,3-dichloropropene of Formula II with (R)-1-(1-naphthyl)ethylamine of Formula III Formula II ClHC=CH-CH₂Cl Formula III H₂N-CH(CH₃)-(naphthyl)

to give a compound of Formula IV;

Formula IV

ClHC=HC-CH₂-NH-CH(CH₃)-(naphthyl)

b) converting the compound of Formula IV to cinacalcet base or pharmaceutically acceptable salts thereof.

A second aspect of the present invention provides a process for preparing cinacalcet base of Formula I and its pharmaceutically acceptable salts. The process comprises the steps of a) reacting a compound of Formula IV with 3-trifluoromethyl phenyl metal halide of Formula V Formula IV ClHC=HC-CH₂-NH-CH(CH₃)-(naphthyl)

-continued

Formula V

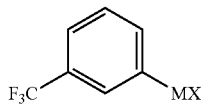

M = Mg
X = F, Cl, Br, to give a compound of Formula VI or salts thereof;

Formula VI

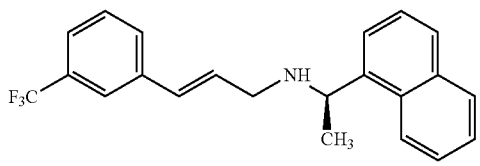

b) reducing the compound of Formula VI or pharmaceutically acceptable salts thereof to cinacalcet base or pharmaceutically acceptable salts thereof.

A third aspect of the present invention provides a process for preparing cinacalcet base of Formula I and its pharmaceutically acceptable salts. The process comprises the steps of a) providing a compound of Formula IV or salts thereof;

Formula IV

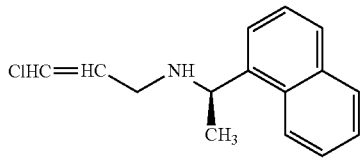

b) converting the compound of Formula IV or salts thereof to compound of Formula VI or pharmaceutically acceptable salt thereof;

c) reducing the compound of Formula VI or pharmaceutically acceptable salts thereof to cinacalcet base or pharmaceutically acceptable salts thereof.

A fourth aspect of the present invention provides a compound of Formula IV or salts thereof Formula IV

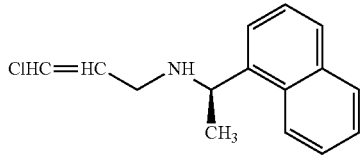

A fifth aspect of the present invention provides a process for preparing cinacalcet base and its pharmaceutically acceptable salts. The process comprises the steps of a) converting 3-(trifluoromethyl)benzaldehyde to 1-[3-(trifluoromethyl)phenyl]prop-2-en-1-ol (Formula VII);

Formula VII

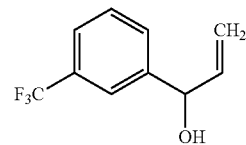

b) converting 1-[3-(trifluoromethyl)phenyl]prop-2-en-1-ol to a compound of Formula IX;

Formula IX

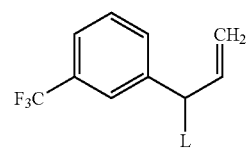

where in 'L' is a leaving group;

c) reacting the compound of Formula IX with (R)-1-(1-naphthyl)ethylamine in the presence of a base to give a compound of Formula VI or pharmaceutically acceptable salts thereof;

Formula VI

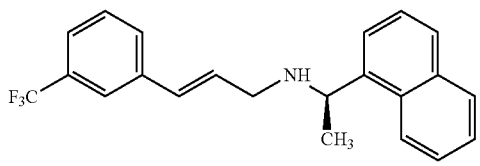

d) reducing the compound of Formula VI or pharmaceutically acceptable salts thereof to cinacalcet base or pharmaceutically acceptable salt thereof.

A sixth aspect of the present invention provides a process for preparing cinacalcet base and pharmaceutically acceptable salts thereof. The process comprises the steps of a) converting 3-[3-(trifluoromethyl)phenyl]prop-2-en-1-ol (Formula VIII)

Formula VIII

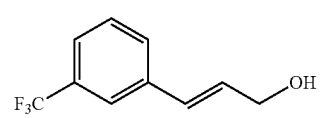

to a compound of Formula X

Formula X

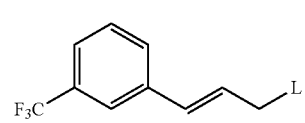

wherein, 'L' is a leaving group; and b) converting the compound of Formula X to cinacalcet base or pharmaceutically acceptable salts thereof.

A seventh aspect of the present invention provides a process for preparing cinacalcet base and its pharmaceutically acceptable salts. The process comprises the steps of a) converting 3-(trifluoromethyl)benzaldehyde to 1-[3-(trifluoromethyl)phenyl]prop-2-en-1-ol (Formula VII);

Formula VII

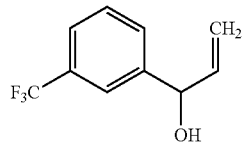

b) isomerising 1-[3-(trifluoromethyl)phenyl]prop-2-en-1-ol to 3-[3-(trifluoromethyl)phenyl]prop-2-en-1-ol (Formula VIII);

Formula VIII

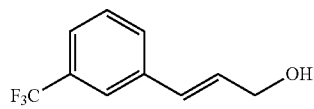

c) converting 3-[3-(trifluoromethyl)phenyl]prop-2-en-1-ol (Formula VIII) to a compound of Formula X;

Formula X

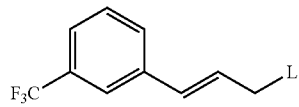

wherein 'L' is a leaving group;

d) reacting the compound of Formula X with (R)-1-(1-naphthyl)ethylamine in the presence of a base to give a compound of Formula VI or pharmaceutically acceptable salts thereof;

Formula VI

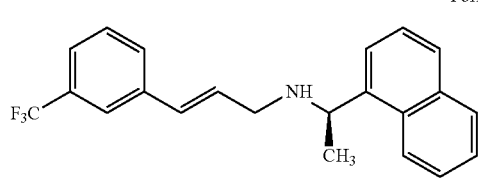

e) reducing the compound of Formula VI or pharmaceutically acceptable salts thereof to cinacalcet base or pharmaceutically acceptable salts thereof.

An eighth aspect of the present invention provides a process for preparing cinacalcet. The process comprises the steps of a) reducing pharmaceutically acceptable salts of a compound of Formula VI Formula VI

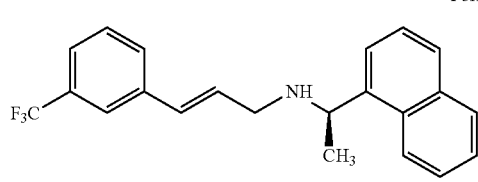

b) isolating cinacalcet in a solvent.

A ninth aspect of the present invention provides a process for preparation of cinacalcet base of Formula I and its pharmaceutically acceptable salts. The process comprises the steps of:

a) providing salt of Formula VI;
b) converting salt of Formula VI to free base;
c) reducing the free base to cinacalcet free base;
d) converting cinacalcet free base to cinacalcet.

Alternatively, the product of step a) can be directly reduced and converted to cinacalcet, characterized in that, the reaction steps a) to d) has been performed in ethylacetate.

A tenth aspect of the present invention provides pharmaceutically acceptable salts of N-[(1R)-1-(naphthalen-1-yl)ethyl]-3-[3-(trifluoromethyl)phenyl]prop-2-en-1-amine of Formula VI in a solid state form Formula VI

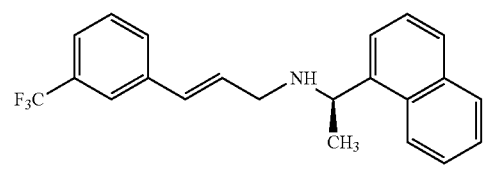

An eleventh aspect of the present invention provides hydrobromide of N-[(1R)-1-(naphthalen-1-yl)ethyl]-3-[3-(trifluoromethyl)phenyl]prop-2-en-1-amine of Formula VI having characteristics d-spacing (Å) values selected from 6.74, 6.20, 5.33, 4.50, 4.30, 3.96, 3.38 or 3.28.

A twelfth aspect of the present invention provides hydrochloride of N-[(1R)-1-(naphthalen-1-yl)ethyl]-3-[3-(trifluoromethyl)phenyl]prop-2-en-1-amine of Formula VI, having characteristics d-spacing (Å) values selected from 6.37, 5.49, 4.77, 4.67, 4.42, 4.25 or 3.67.

A thirteenth aspect of the present invention provides fumarate of N-[(1R)-1-(naphthalen-1-yl)ethyl]-3-[3-(trifluoromethyl)phenyl]prop-2-en-1-amine of Formula VI.

Formula VIa

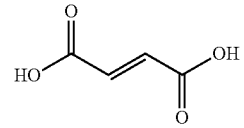

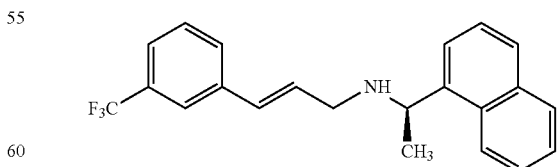

A fourteenth aspect of the present invention provides citrate of N-[(1R)-1-(naphthalen-1-yl)ethyl]-3-[3-(trifluoromethyl)phenyl]prop-2-en-1-amine of Formula VI

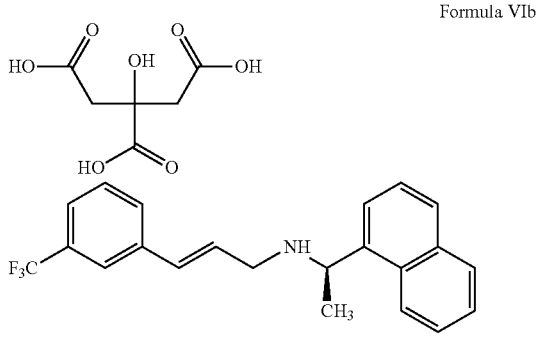

Formula VIb

A fifteenth aspect of the present invention provides pure cinacalcet, wherein cinacalcet has purity more than 98%, preferably more than 99% and more preferably more than 99.5% when determined by HPLC.

A sixteenth aspect of the present invention provides cinacalcet having a compound of Formula VI, wherein the content of the compound of Formula VI is less than 0.10%, preferably less than 0.05% and more preferably not detectable when determined by HPLC.

A seventeenth aspect of the present invention provides cinacalcet free of an impurity at RRT 1.72 when determined by HPLC.

An eighteenth aspect of the present invention provides pharmaceutical composition comprising one or more salts of N-[(1R)-1-(naphthalen-1-yl)ethyl]-3-[3-(trifluoromethyl)phenyl]prop-2-en-1-amine and pharmaceutically acceptable excipients.

A nineteenth aspect of the present invention provides a method for treating a subject in need of an inorganic ion receptor-modulating compound wherein, inorganic ion receptor-modulating compound can be selected from one or more salts of N-[(1R)-1-(naphthalen-1-yl)ethyl]-3-[3-(trifluoromethyl)phenyl]prop-2-en-1-amine.

BRIEF DESCRIPTION OF THE DRAWINGS

FIG. 11: Table 1: Peak table for FIG. 1.
FIG. 12: Table 2: Peak table for FIG. 4.
FIG. 13: Table 3: Peak table for FIG. 5.
FIG. 14: Table 4: Peak table for FIG. 8.

DETAILED DESCRIPTION OF THE INVENTION

Figure 1:
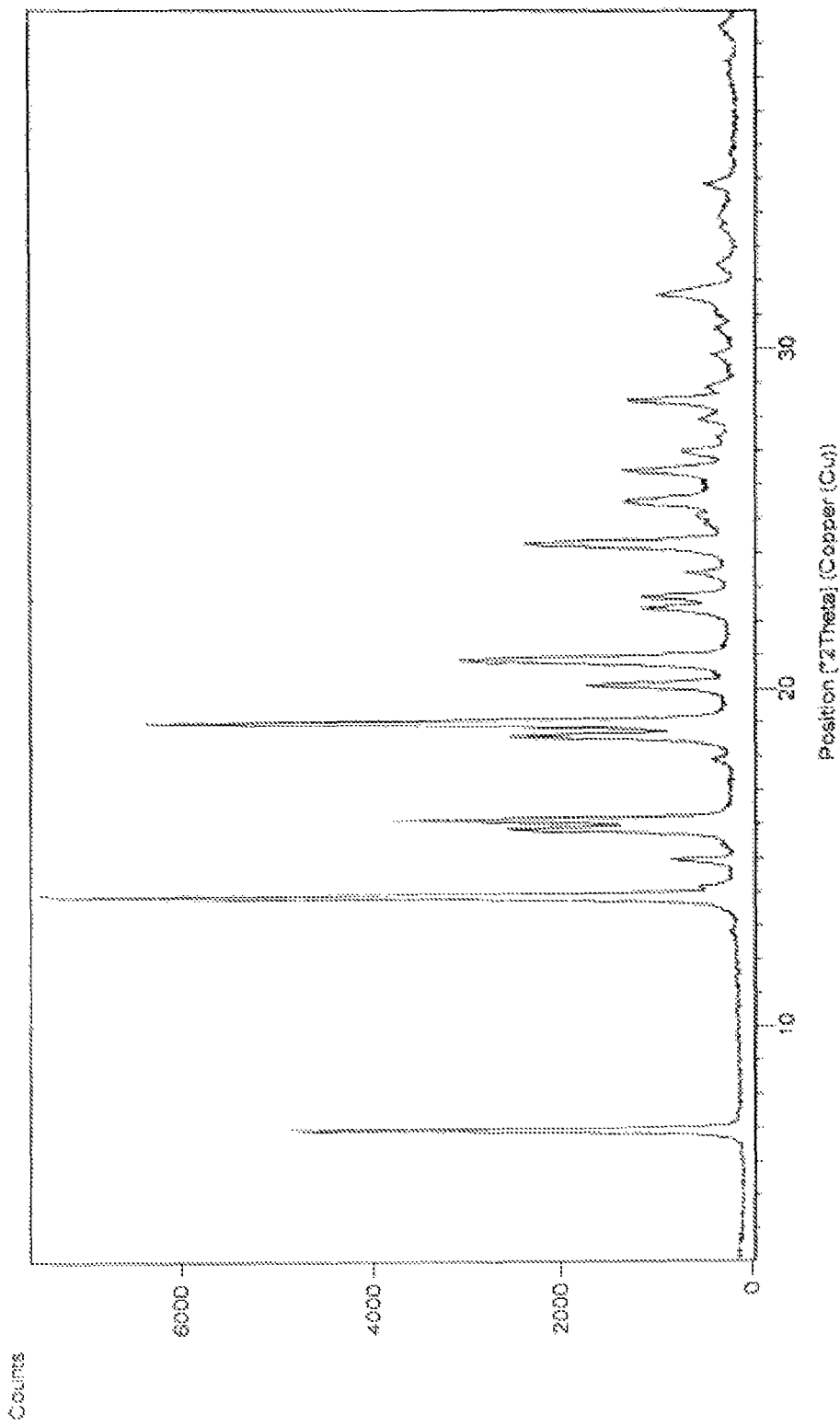
FIG. 1: X-ray diffraction pattern (XRD) of N-[(1R)-1-(naphthalen-1-yl)ethyl]-3-[3-(trifluoromethyl)phenyl]prop-2-en-1-amine hydrochloride.

The present invention provides intermediates and processes for preparing cinacalcet base, its derivatives and pharmaceutically acceptable salts.

Various embodiments and variants of the present invention are provided below:

In an embodiment 3-chloro-N-[(1R)-1-(naphthalen-1-yl)ethyl]prop-2-en-1-amine of Formula IV can be prepared by reacting 1,3-dichloropropene with (R)-1-(1-naphthyl)ethylamine in at least one organic solvent in the presence of a base. The base used in this process can be selected from alkali metal hydroxides (e.g., sodium hydroxide, potassium hydroxide or the like); alkali metal carbonates (e.g., sodium carbonate, potassium carbonate or the like); alkali metal alkoxides (e.g., sodium methoxide, sodium ethoxide, potassium t-butoxide or the like) or a mixture thereof. The solvent used in this process can be selected from aromatic hydrocarbons (e.g., benzene, toluene, xylene or the like); aliphatic hydrocarbons (e.g., hexane, cyclohexane, heptane or the like); ethers (e.g., diethylethers, diisopropylether or the like); ketones (e.g., methylisobutylketone, acetone or the like); alcohols (e.g., methanol, ethanol, 2-propanol, n-butanol or the like); amides (e.g., N,N-dimethylformamide, N-methyl-2-pyrrolidine or the like); sulfoxides (e.g., dimethylsulfoxide or the like); nitriles (e.g., acetonitrile, propanonitrile or the like) or a mixture thereof.

The reaction between 1,3-dichloropropene and (R)-1-(1-naphthyl)ethylamine can also be carried out in a heterogeneous mixture of solvents wherein one solvent is water and the other is selected from aromatic hydrocarbons (e.g., benzene, toluene, xylene or the like); aliphatic hydrocarbons (e.g., hexane, cyclohexane, heptane or the like); ethers (e.g., diethylethers, diisopropylether or the like); ketones (e.g., methylisobutylketone, acetone or the like); alcohols (e.g., methanol, ethanol, 2-propanol, n-butanol or the like); amides (e.g., N,N-dimethylformamide, N-methyl-2-pyrrolidine or the like); sulfoxides (e.g., dimethylsulfoxide or the like) or nitriles (e.g., acetonitrile, propanonitrile or the like) in the presence of phase transfer catalyst. The phase transfer catalyst used can be selected from quaternary ammonium salts (e.g., tetra-n-butyl ammonium bromide, methyltrioctylammonium chloride or the like) or crown ethers (e.g., 12-crown-4, 15-crown-5, 18-crown-6, dibenzo-18-crown-6, and diaza-18-crown-6).

3-Chloro-N-[(1R)-1-(naphthalen-1-yl)ethyl]prop-2-en-1-amine of Formula IV thus obtained can be converted into its salt by treating it with acid, wherein the acid can be selected from inorganic acids (e.g., hydrochloric, hydrobromic or sulfuric acid) or organic acid (e.g., acetic acid, lactic acid, malonic acid, citric acid, quinic acid, succinic acid, oxalic acid, maleic acid, tartaric acid, camphor sulfonic acid or formic acid). In a particular embodiment, a compound of Formula IV is isolated as the hydrochloride salt.

A salt of the compound of Formula IV can be converted to its free base by treating it with a base for further chemical transformation, wherein the base can be selected from alkali metal hydroxides (e.g., sodium hydroxide, potassium hydroxide or the like) or alkali metal carbonates (e.g., sodium carbonate, potassium carbonate or the like).

In another embodiment, a compound of Formula IV reacts with 3-trifluoromethyl phenyl metal halides in a solvent in the presence of catalytic metal salt or metal complex and a stabilizing agent. 3-trifluoromethylphenyl metal halide can be selected from 3-trifluoromethylphenyl magnesium halide (e.g., 3-trifluoromethylphenyl magnesium chloride, 3-trifluoromethylphenyl magnesium bromide or the like), 3-trifluoromethylphenyl zinc halide (e.g., 3-trifluoromethylphenyl zinc chloride or 3-trifluoromethylphenyl zinc bromide or the like) or 3-trifluoromethylphenyl lithium. The solvent used in the step can be selected from ethers such as tetrahydrofuran, dioxane or mixture thereof. The metal salt or metal complex can be selected from iron (e.g., iron trichloride, iron acetyl acetonate, iron benzoyl acetonate and the like), nickel [e.g., nickel acetyl acetonate, dichloronickel(1,2-diphenylphosphinoethane) or the like)] or palladium [e.g., dichloropalladium (1,2-diphenylphosphinoethane) or the like] salt or an iron, nickel or palladium complex with tertiary phosphines or ditertiary diphosphines (e.g., triphenylphosphine, tricyclohexylphosphine, 1,2-diphenylphosphinoethane, 1,2-diphenylphosphinopropane, 1,2-diphenylphosphinofuran, or 1,2-diphenylphosphinobutane). The stabilizing agent used in the step can be selected from polar aprotic solvent (e.g., 1,3-dimethyl-3,4,5,6-tetrahydro-2(1H)-pyrimidinone; DMPU, N-methyl-2-pyrrolidone, N,N-dimethylformamide, N,N-dimethylacetamide or N-methyl-morpholine), amines (e.g., triethylamine or tetramethylethylenediamine) or a mixture thereof.

In another embodiment, a compound of Formula VI or pharmaceutically acceptable salts thereof can be prepared by reacting a compound of Formula IX or X (wherein 'L' represents a leaving group) with (R)-1-(1-naphthyl)ethylamine in the presence of one or more bases in one or more solvents. The base used in this step can be selected from organic base (e.g., triethylamine, isopropylethylamine or diisopropylamine), inorganic base (e.g., sodium carbonate, potassium carbonate, sodium bicarbonate or potassium bicarbonate) or a mixture thereof in a solvent selected from $C_3$-$C_6$ ketones, $C_6$-$C_8$ aromatic hydrocarbon, $C_3$-$C_6$ esters (methyl acetate, ethyl acetate or a mixture thereof), $C_2$-$C_6$ alcohol, $C_2$-$C_7$ ether, dimethylacetamide, dimethylsulfoxide, dimethylformamide, N-methylpyrrolidine, acetonitrile, water or a mixture thereof.

The compound of Formula IX or X can be prepared by converting hydroxyl group of the compound of Formula VII or VIII to a leaving group using a reagent known to a person of ordinary skill in the art. The reagent used to convert hydroxyl moiety to a leaving group can be selected from thionyl halide, aliphatic sulfonyl halide or aromatic sulfonyl halide. In another embodiment, the reagent is selected from thionyl chloride, thionyl bromide, methanesulfonyl chloride, benzenesulfonyl chloride, 4-nitrobenzensulfonylchloride, or p-toluenesulfonyl chloride. The solvents used in this step can be selected from chlorinated aliphatic hydrocarbon, $C_2$-$C_6$ ether, $C_6$-$C_8$ aromatic hydrocarbon, acetonitrile or a mixture thereof.

1-[3-(trifluoromethyl)phenyl]prop-2-en-1-ol of Formula VII can be prepared by processes already known to a person of ordinary skill in art including, for example, treating 3-(trifluoromethyl)benzaldehyde with vinyllic reagent in ether. The vinyllic reagents can be selected from vinyl lithium, vinyl borates, vinyl zinc halide, divinylzinc or vinyl magnesium halide.

1-[3-(trifluoromethyl)phenyl]prop-2-en-1-ol of Formula VII isomerizes to 3-[3-(trifluoromethyl)phenyl]prop-2-en-1-ol of Formula VIII in the presence of one or more acids in one or more solvents. The acid employed in this step can be selected from organic acids (e.g., acetic acid, formic acid, camphor sulfonic acid, methane sulfonic acid, trifluoromethanesulfonic acid, dichloroacetic acid, trichloroacetic acid, trifluoroacetic acid) or mineral acid (e.g., hydrochloric acid, sulfuric acid, phosphoric acid).

The compound of Formula VII may contain 0-50% of compound of Formula VIII and vice versa.

The solvent employed for isomerization of alcohol of Formula VII to an alcohol of Formula VIII can be selected from ethers (e.g., diethylether, diisopropylethers, methyl tertiary butyl ether, tetrahydrofuran or a mixture thereof), esters (e.g., methyl acetate, ethyl acetate or a mixture thereof), nitriles (e.g., acetonitrile, propanitrile or a mixture thereof), ketones (e.g., acetone, diethylketone, methylethylketone or mixtures thereof) and dimethylformamide, dimethylsulfoxide or a mixture thereof.

The compound of Formula VI can be isolated in solid state forms as salts. Some examples of the salts that can be isolated are hydrochloride, hydrobromide, hydroiodide, sulfate, acetate, lactate, salicylate, citrate, tartrate, pantothenate, bitartrate, ascorbate, oxalate, malonate, succinate, maleate, fumarate, gluconate, glucaronate, saccharate, formate, benzoate, glutamate, methanesulfonate, ethanesulfonate, benzensulfonate, p-toluenesulfonate or camphor sulfonate.

The solid state form can be amorphous, crystalline or mixture thereof.

Hydrochloride salt of compound of Formula V can be re-crystallized from organic solvent, wherein the solvent can be selected from alcohol (e.g., methanol, ethanol, n-propanol, isopropanol, n-butanol, isobutanol or t-butanol), ethers (diethylether, diisopropylether, methyl t-butyl ether, tetrahydrofuran, dioxane or the like), ester (ethylacetate, propylacetate, n-butylacetate, isobutyl acetate or the like), ketone (e.g., acetone, methylethyl ketone or the like), alkanes (e.g., hexane, hexanes, n-heptane or the like) or a mixture thereof.

The hydrochloride salt of N-[(1R)-1-(naphthalen-1-yl) ethyl]-3-[3-(trifluoromethyl)phenyl]prop-2-en-1-amine isolated in the solid form can be characterized by d-spacing (Å) values selected from 12.69, 6.37, 6.24, 5.92, 5.58, 5.49, 4.95, 4.77, 4.67, 4.42, 4.25, 3.97, 3.92, 3.80, 3.67, 3.55, 3.49, 3.38, 3.30, 3.20, 3.14, 3.09, 2.99, 2.92, 2.83, 2.76, 2.64, 2.58 or 2.35 and the corresponding 2-theta values selected from 6.97, 13.90, 14.20, 14.98, 15.88, 16.16, 17.92, 18.62, 19.01, 20.08, 20.89, 22.37, 22.71, 23.43, 24.27, 25.07, 25.51, 26.40, 26.95, 27.91, 28.46, 28.88, 29.84, 30.63, 31.57, 32.45, 33.91, 34.84 or 38.30±0.02.

Figure 2:
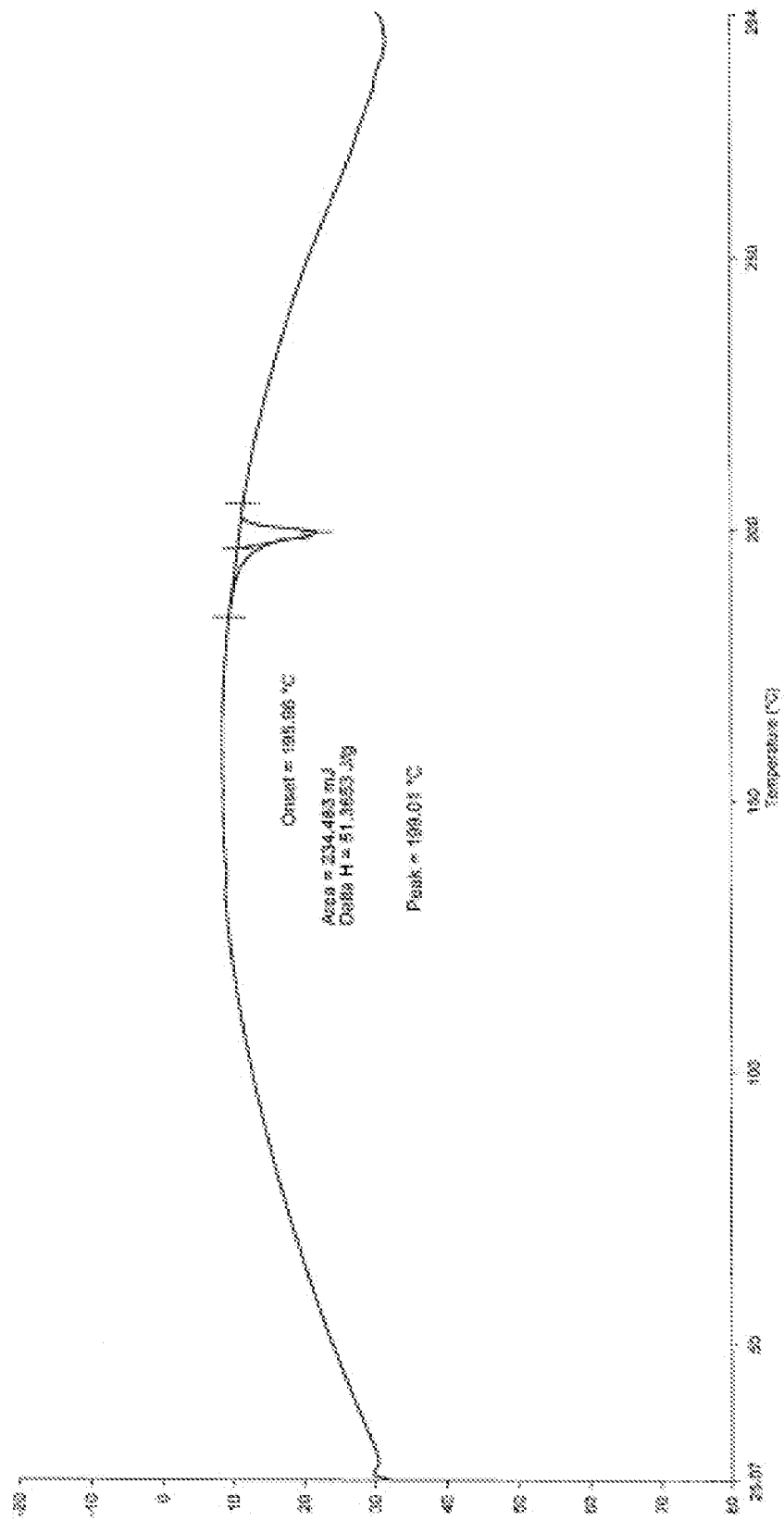
FIG. 2: Differential Scanning calorimetry (DSC) thermo gram of N-[(1R)-1-(naphthalen-1-yl)ethyl]-3-[3-(trifluoromethyl)phenyl]prop-2-en-1-amine hydrochloride.
Figure 3:
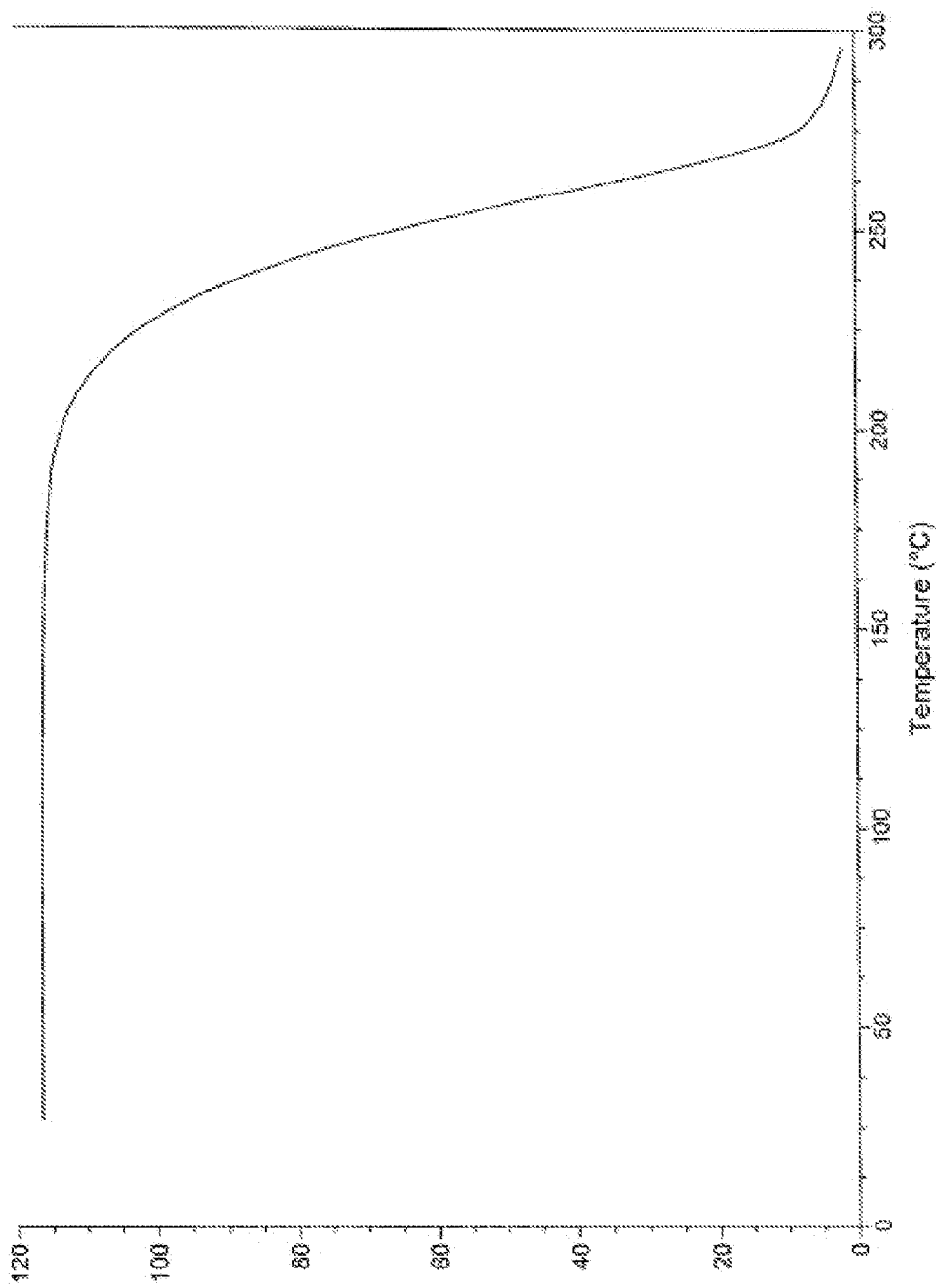
FIG. 3: Thermal Gravimetric Analysis (TGA) thermo gram of N-[(1R)-1-(naphthalen-1-yl)ethyl]-3-[3-(trifluoromethyl)phenyl]prop-2-en-1-amine hydrochloride.

Hydrochloride salt of N-[(1R)-1-(naphthalen-1-yl)ethyl]-3-[3-(trifluoromethyl)phenyl]prop-2-en-1-amine can also be characterized by one or more of the following:
  a) XRD pattern substantially as depicted in FIG. 1;
  b) DSC substantially the same pattern as depicted in FIG. 2, wherein DSC shows an endothermic peak at 199.01° C.;
  c) TGA substantially the same as depicted in FIG. 3.

The compound of Formula VI can also be isolated as hydrobromide salt in a solid state form wherein, the solid state form can be amorphous, crystalline or mixture thereof.

Figure 4:
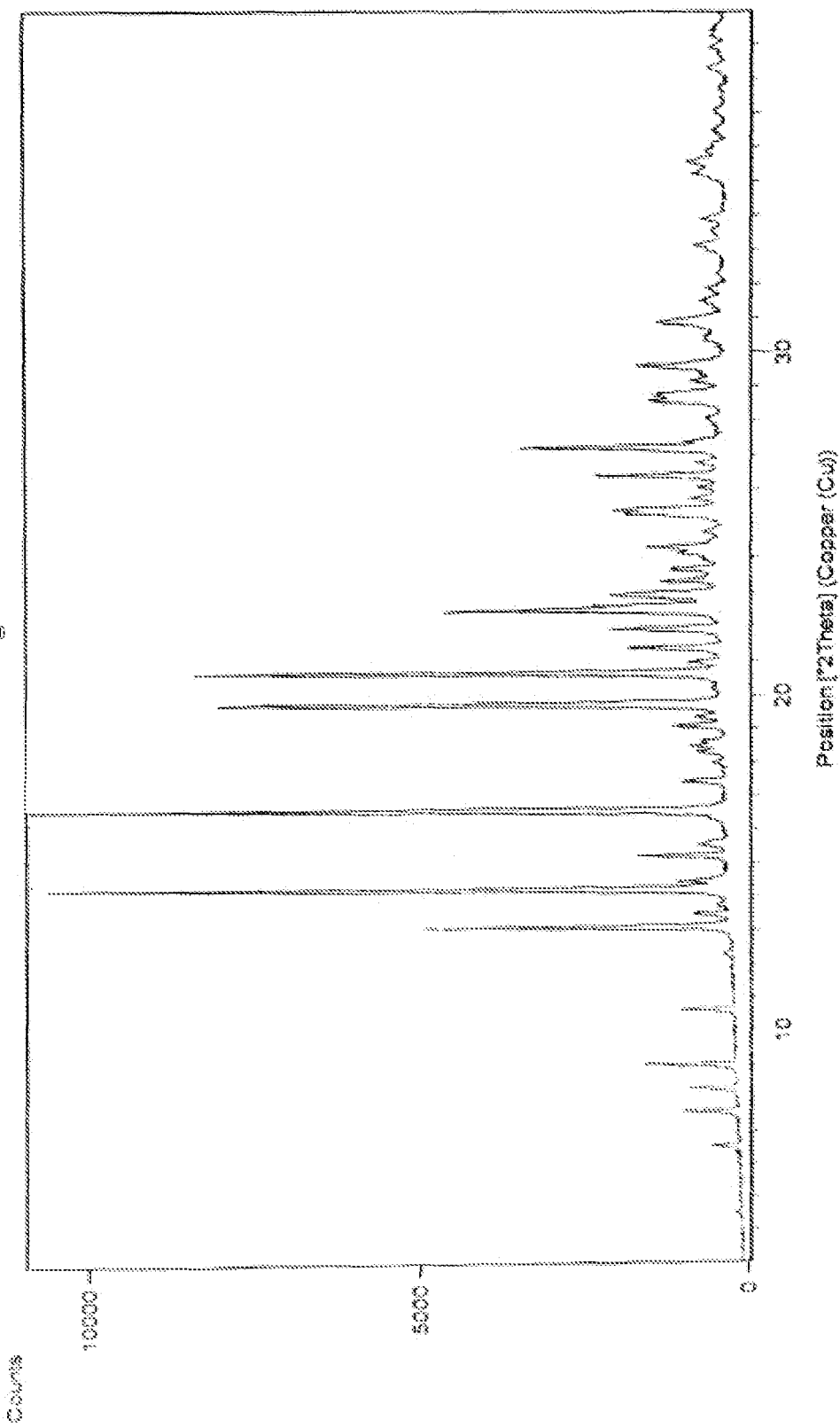
FIG. 4: XRD of N-[(1R)-1-(naphthalen-1-yl)ethyl]-3-[3-(trifluoromethyl)phenyl]prop-2-en-1-amine hydrobromide.

The hydrobromide salt of Formula VI, isolated in crystalline form can be characterized by d-spacing (Å) values selected from 6.74, 6.20, 5.33, 4.50, 4.30, 3.96, 3.38 or 3.28 and the corresponding 2-theta values selected from 13.12, 14.28, 16.61, 19.74, 20.65, 22.46, 26.31 or 27.20±0.02 as depicted in FIG. 4.

The fumarate salt of N-[(1R)-1-(naphthalen-1-yl)ethyl]-3-[3-(trifluoromethyl)phenyl]prop-2-en-1-amine can be characterized by d-spacing values in (Å) selected from 16.43, 11.00, 9.10, 8.24, 7.49, 7.20, 6.59, 6.28, 6.10, 5.53, 5.36, 5.19, 5.03, 4.72, 4.66, 4.54, 4.22, 4.11, 3.97, 3.91, 3.86, 3.77, 3.67, 3.50, 3.39, 3.30, 3.11, 3.00, 2.83, 2.76, 2.69, 2.54 or 2.37; and the corresponding 2-theta values selected from 5.38, 8.04, 9.72, 10.73, 11.82, 12.30, 13.43, 14.10, 14.52, 16.03, 16.53, 17.08, 17.62, 18.81, 19.04, 19.56, 21.06, 21.61, 22.24, 22.77, 23.02, 23.59, 24.20, 25.49, 26.32, 27.01, 28.74, 29.80, 31.66, 32.40, 33.27, 35.32 or 38.00±0.02°.

Figure 5:
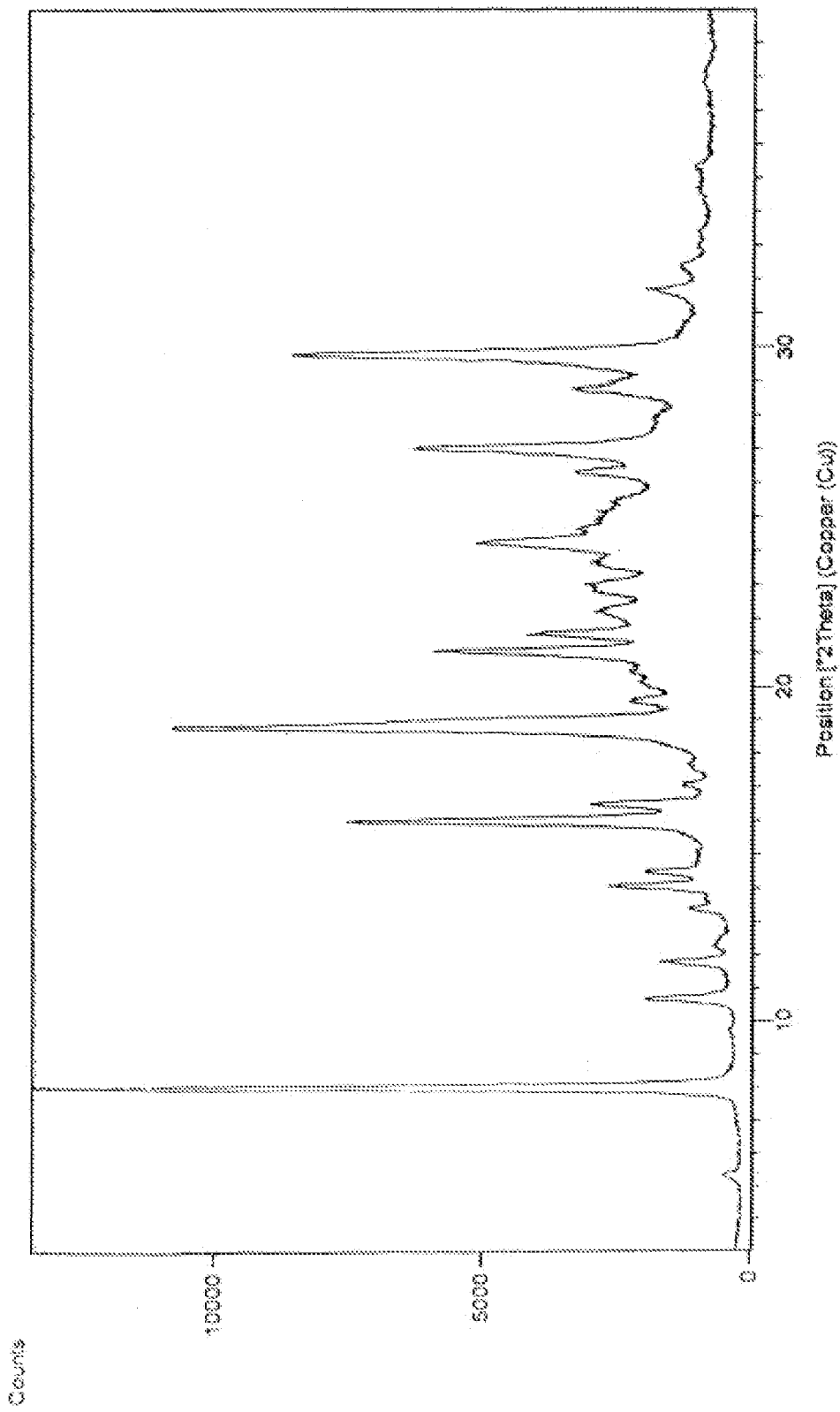
FIG. 5: XRD of N-[(1R)-1-(naphthalen-1-yl)ethyl]-3-[3-(trifluoromethyl)phenyl]prop-2-en-1-amine fumarate.
Figure 6:
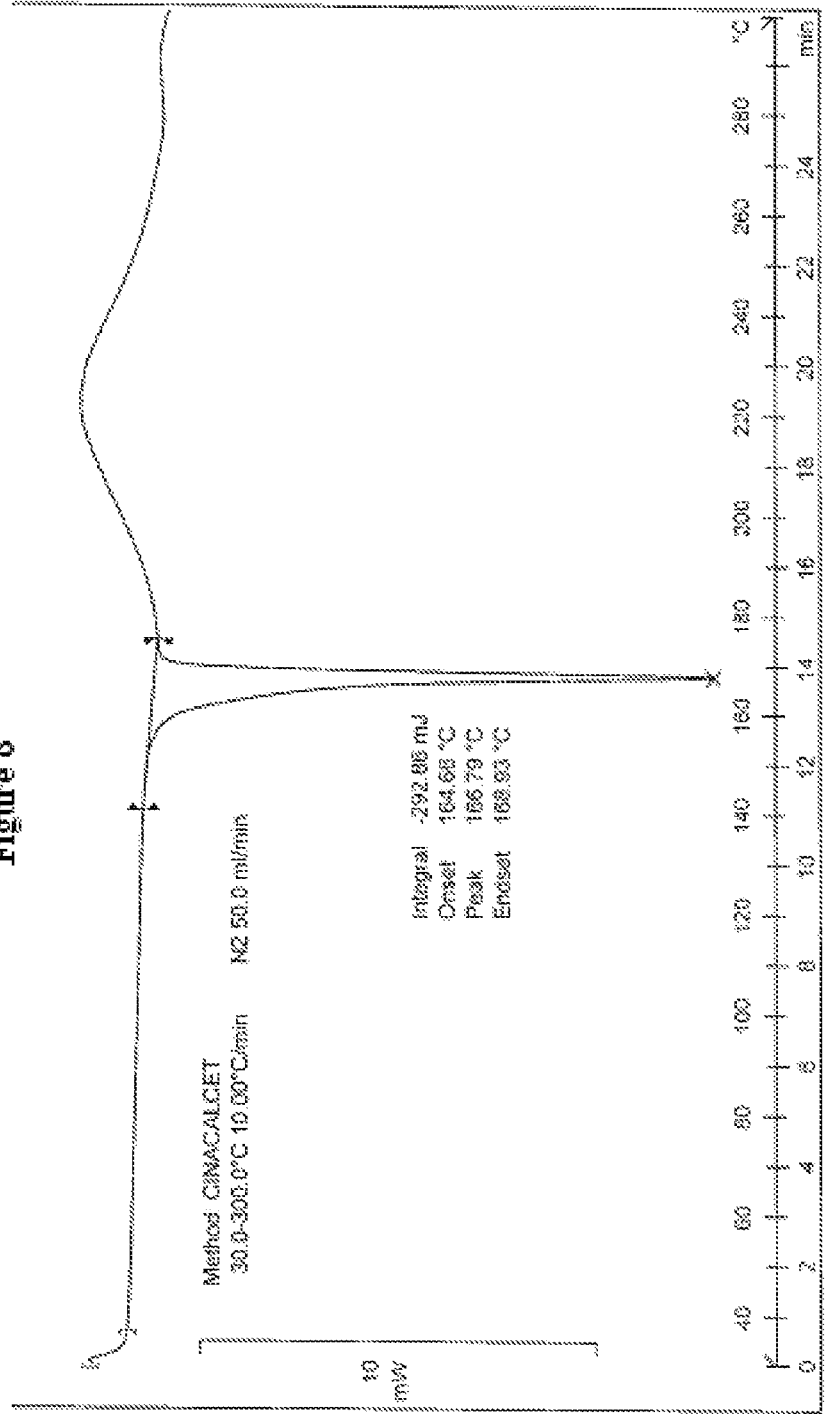
FIG. 6: DSC thermo gram of N-[(1R)-1-(naphthalen-1-yl)ethyl]-3-[3-(trifluoromethyl)phenyl]prop-2-en-1-amine fumarate.
Figure 7:
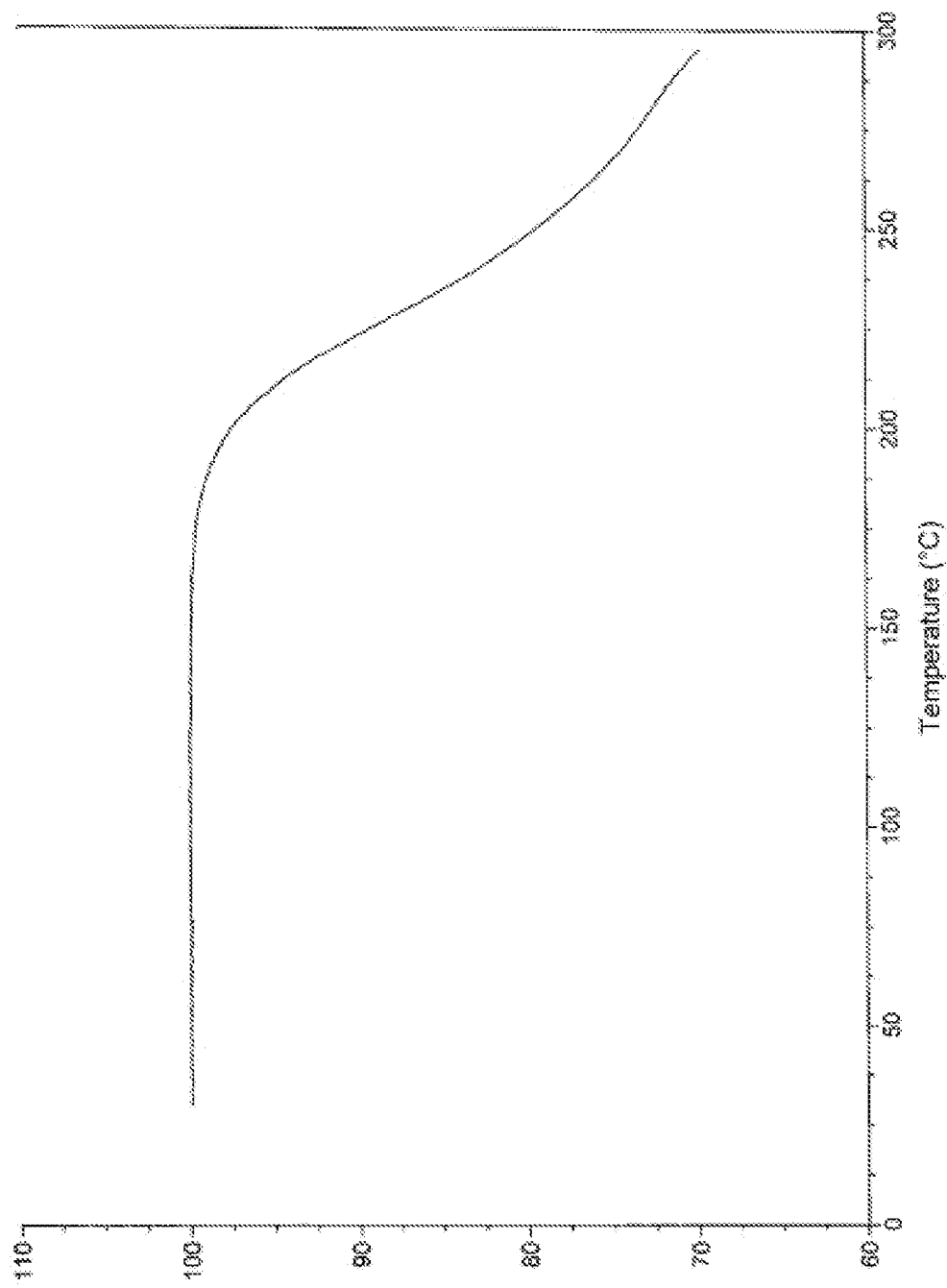
FIG. 7: TGA thermo gram of N-[(1R)-1-(naphthalen-1-yl)ethyl]-3-[3-(trifluoromethyl)phenyl]prop-2-en-1-amine fumarate.

The fumarate salt of N-[(1R)-1-(naphthalen-1-yl)ethyl]-3-[3-(trifluoromethyl)phenyl]prop-2-en-1-amine can also be characterized by one or more of the following:
  a) XRD pattern substantially the same as depicted in FIG. 5;
  b) DSC having substantially the same pattern as depicted in FIG. 6, wherein DSC shows an endothermic peak at 166.79° C.;
  c) TGA having substantially the same pattern as depicted in FIG. 7.

The citrate salt of N-[(1R)-1-(naphthalen-1-yl)ethyl]-3-[3-(trifluoromethyl)phenyl]prop-2-en-1-amine can be characterized by d-spacing values in (Å) selected from 23.68, 11.86, 7.91, 7.49, 7.35, 6.93, 6.64, 6.42, 6.08, 5.66, 5.45, 5.35, 5.12, 5.02, 4.89, 4.84, 4.74, 4.65, 4.41, 4.16, 4.09, 3.91, 3.86, 3.75, 3.72, 3.58, 3.55, 3.48, 3.46, 3.64, 3.32, 3.18, 3.07, 2.83, 2.75, 2.69, 2.60, 2.45, 2.42, 2.37 or 2.32; and the corresponding 2-theta values selected from 3.73, 7.46, 11.18, 11.82, 12.04, 12.77, 13.34, 13.78, 14.56, 15.66, 16.28, 16.57, 17.31, 17.67, 18.13, 18.34, 18.74, 19.10, 20.13, 21.36, 21.75, 22.76, 23.03, 23.72, 23.91, 24.90, 25.08, 25.59, 25.76, 26.50, 26.89, 28.09, 29.12, 31.61, 32.62, 33.35, 34.46, 36.71, 37.15, 37.94 or 38.80±0.02°.

Figure 8:
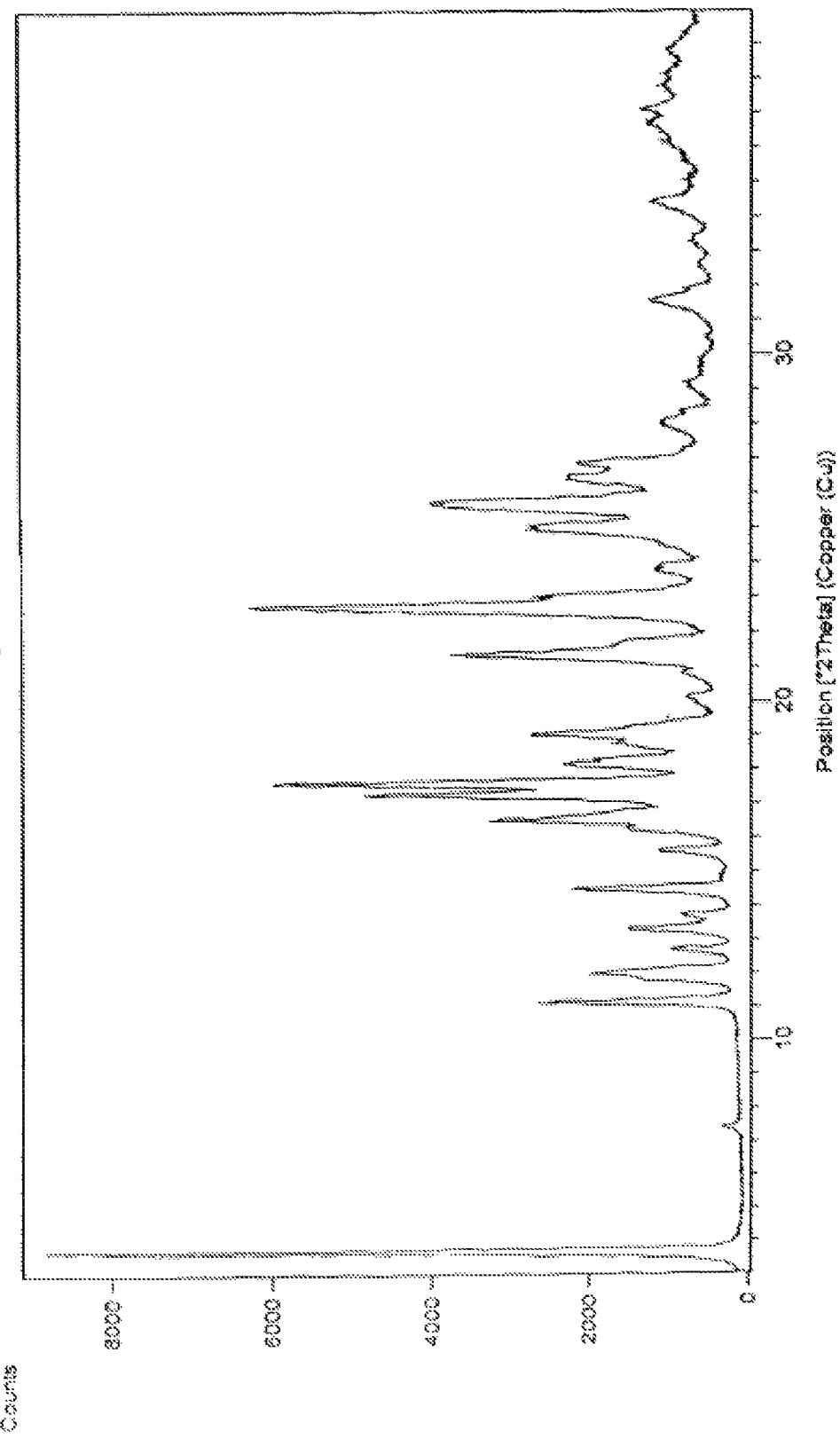
FIG. 8: X-ray diffraction pattern (XRD) of N-[(1R)-1-(naphthalen-1-yl)ethyl]-3-[3-(trifluoromethyl)phenyl]prop-2-en-1-amine citrate.
Figure 9:
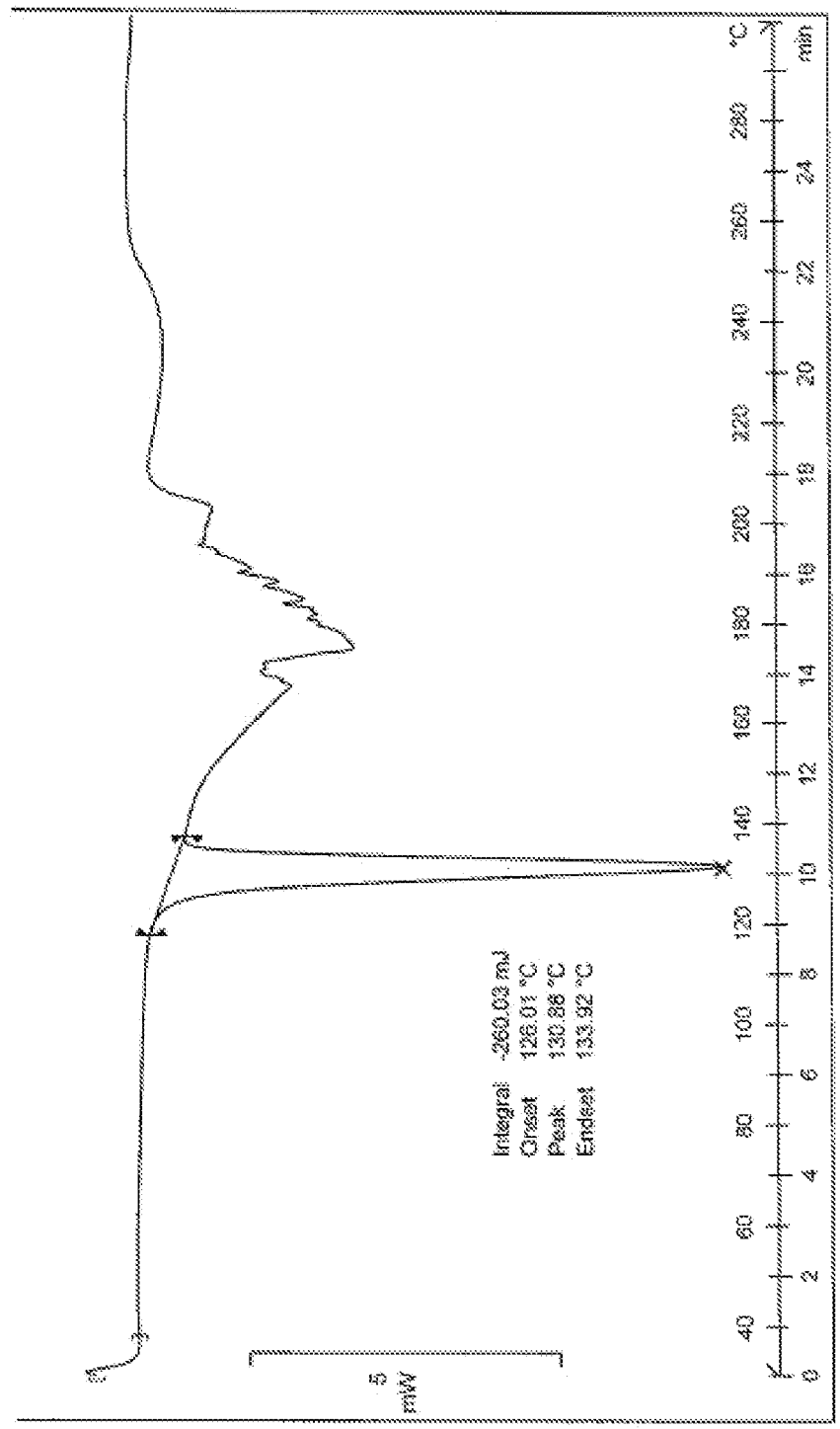
FIG. 9: DSC thermo gram of N-[(1R)-1-(naphthalen-1-yl)ethyl]-3-[3-(trifluoromethyl)phenyl]prop-2-en-1-amine citrate.
Figure 10:
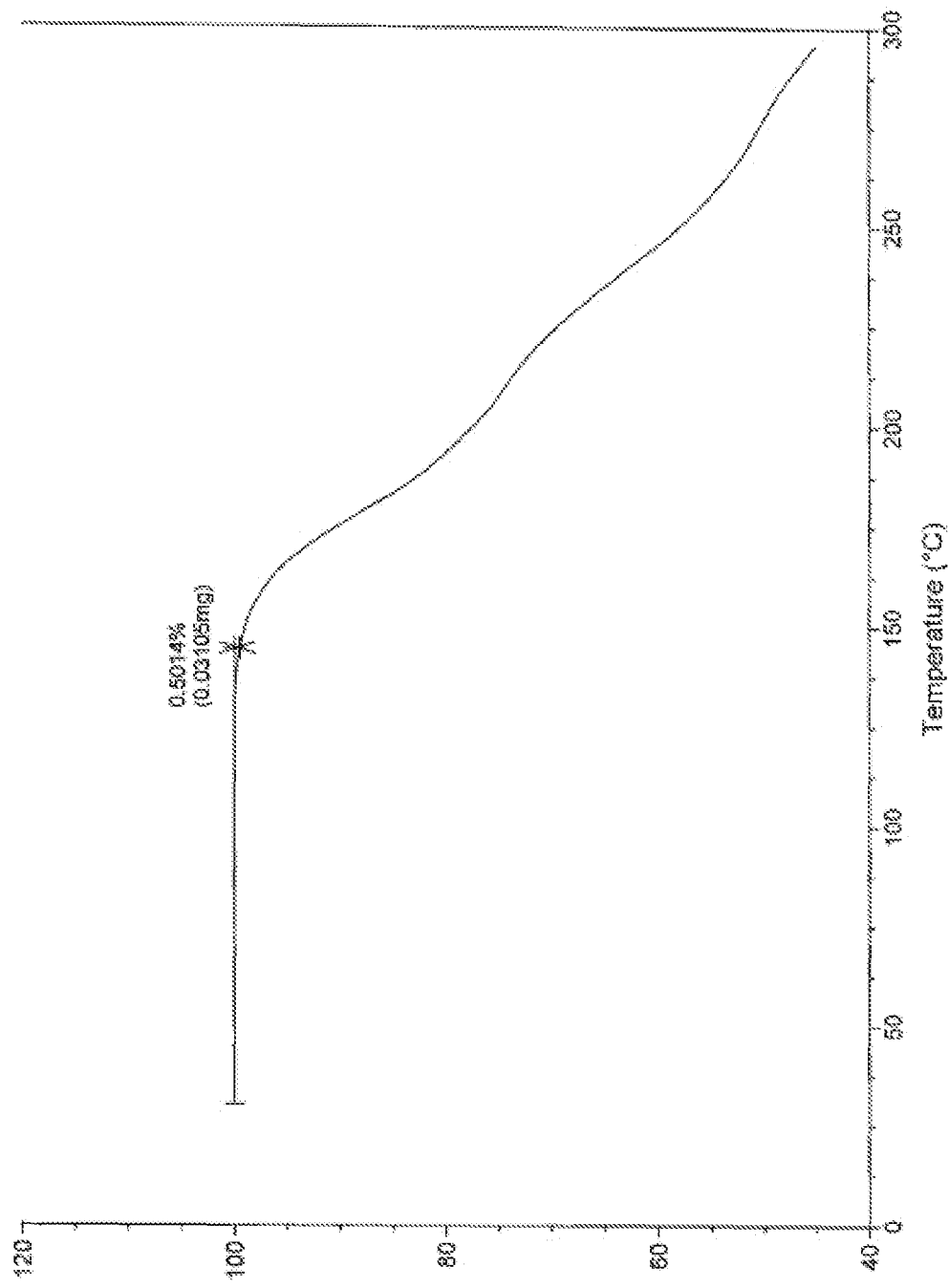
FIG. 10: TGA thermo gram of N-[(1R)-1-(naphthalen-1-yl)ethyl]-3-[3-(trifluoromethyl)phenyl]prop-2-en-1-amine citrate.

The citrate salt N-[(1R)-1-(naphthalen-1-yl)ethyl]-3-[3-(trifluoromethyl)phenyl]prop-2-en-1-amine can be characterized can also be characterized by one or more of the following:
  a) XRD pattern substantially the same as given in FIG. 8;
  b) DSC having substantially the same pattern as depicted in FIG. 9, wherein DSC shows an endothermic peak at 130.88° C.;
  c) TGA having substantially the same pattern as depicted in FIG. 10.

The present invention provides a process for preparing cinacalcet comprising the steps of
  a) reducing pharmaceutically acceptable salts of a compound of Formula VI

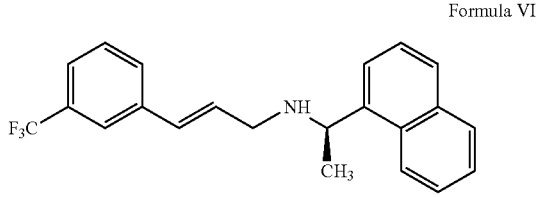

Formula VI b) isolating cinacalcet in a solvent.

Cinacalcet can be isolated in a solvent or a mixture of solvents in which cinacalcet has low solubility. Solvents in which cinacalcet has low solubility includes, but are not limited to water, a $C_3$-$C_6$ ketone, a $C_5$-$C_8$ aliphatic or aromatic hydrocarbon, $C_3$-$C_6$ ester, a $C_2$-$C_6$ alcohol, $C_2$-$C_7$ ethers, dimethylacetamide, dimethylsulfoxide, dimethylformamide, N-methylpyrrolidine, acetonitrile and a mixture thereof. The solvent can be selected from water, acetone, diethylether, tert-butylethylether, n-pentane, n-hexane, hexanes, ethylacetate, isopropylacetate, toluene, methyl-t-butyl ether or cyclohexane.

The salts of Formula VI are converted to cinacalcet by a process comprising the steps of:
  a) providing salt of Formula VI;
  b) converting salt of Formula VI to free base;
  c) reducing the free base to cinacalcet free base;
  d) converting cinacalcet free base to cinacalcet.

According to one approach, salts of Formula VI can be treated with a base to give free base of compound of Formula V, which can be reduced to cinacalcet free base and further converted to cinacalcet (hydrochloride salt) by following any method known to a person of ordinary skill in the art, including, for example, the procedure described in the instant application. According to another approach, a salt of Formula VI can directly be reduced to salt of Formula I, which can then be converted to cinacalcet by known methods or the one described in instant application. In a particular embodiment, the reactions pertaining to both of the approaches can be carried out in ethyl acetate.

Alternatively, the product of step a) can be directly reduced and converted to cinacalcet, characterized in that, the reaction steps a) to d) has been performed in ethylacetate.

The term "reduction" referred to in this application, may involve hydrogenation using hydrogen source in the presence of a catalyst or a reducing agent. Catalytic reduction can be carried out in one or more solvents selected from water, alcohols (e.g., methanol, ethanol, n-propanol, isopropanol or the like), acids (e.g., acetic acid or the like), esters (e.g., ethyl acetate or the like) or a mixture thereof. The catalyst used in the reduction may be selected from palladium, platinum, or Raney nickel. The reducing agents used in the reaction can be selected from boranes or metal hydrides (sodium hydride, sodium borohydride, lithium aluminum hydride, Diisobutylaluminum hydride, Vitride® or the like).

In another embodiment, the reaction of 1,3-dichloropropene with (R)-1-(1-naphthyl)ethylamine yields an impurity of Formula XI

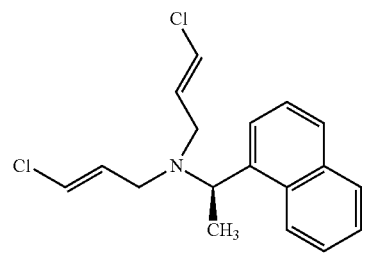

Formula XI

The impurity of Formula XI may be characterized by $^1$H NMR spectrum having chemical shifts at about 8.3, 7.8, 7.7, 7.5, 6.0, 4.5, 3.2, and 1.4 ppm; a $^{13}$C NMR spectrum having carbon chemical shifts at about 139.76, 134.09, 131.54, 130.80, 128.78, 127.77, 125.67, 125.47, 125.26, 124.58, 124.01, 119.83, 56.65, 49.72, and 17.70 and by a retention time ("RT") of about 47.5 minutes in HPLC or relative retention time ("RRT") of about 1.72.

The present invention provides pure cinacalcet, wherein cinacalcet has purity more than 98%, preferably more than 99% and more preferably more than 99.5% when determined by HPLC.

The present invention provides cinacalcet free of a compound of Formula VI, wherein the content of the compound of Formula VI is less than 0.10%, preferably less than 0.05% and more preferably not detectable when determined by HPLC.

Another aspect of the present invention provides cinacalcet having bulk density ranging from 0.15-0.25 g/mL and tapped density ranging from 0.40-0.50 g/mL.

Another aspect of the present invention provides cinacalcet having $D_{90}$ ranging from 0-100 μm.

The present invention provides pharmaceutical composition comprising salts of N-[(1R)-1-(naphthalen-1-yl)ethyl]-3-[3-(trifluoromethyl)phenyl]prop-2-en-1-amine.

The pharmaceutical composition of the present invention may be formulated in a conventional manner which includes powders, tablets, pills, capsules, catchets and dispersible granules using one or more pharmaceutically acceptable excipients.

The compositions can be administered by different routes including intravenously, intraperitoneal, subcutaneous and intramuscular, orally, topically or transmucosally.

The present invention provides a method of treating a subject in need of an inorganic ion receptor-modulating compound, wherein the ion receptor-modulating compound is selected from one or more salts of N-[(1R)-1-(naphthalen-1-yl)ethyl]-3-[3-(trifluoromethyl)phenyl]prop-2-en-1-amine.

In a preferred embodiment, the present invention provides a method of treating a subject in need of calcimimetic, comprising administering a therapeutically effective amount of one or more salts of N-[(1R)-1-(naphthalen-1-yl)ethyl]-3-[3-(trifluoromethyl)phenyl]prop-2-en-1-amine, wherein the need of calcimimetic arises due to hyperparathyroidism and the said therapeutically effective amount decreases the levels of parathyroid hormone in a said subject.

The term "room temperature" as used in the present invention refers to a temperature range of 25° C. to 30° C.

The term "providing" as used in the present invention refers to preparing a compound by any process known to the person ordinary skill in the art including for example, the process as described herein.

The term "isolating" as used in the present invention refers to technique used for isolating the solid compound from the solution, known to the person skilled in the art such as decanting, precipitating, filtering, centrifuging, evaporating, distilling, cooling or concentrating the solvent to obtain solid compound.

The term, "pharmaceutically acceptable salts" as used in the present invention refers to the acid addition salts of a compound, wherein acid can be selected from mineral acids (e.g., hydrochloric acid, hydrobromic acid or phosphoric acid) or organic acids (e.g., formic acid, acetic acid, lactic acid, malonic acid, citric acid, quinic acid, succinic acid, oxalic acid, maleic acid, tartaric acid, fumaric acid, or camphor sulfonic acid).

The term "pharmaceutically acceptable excipients" as used in the present invention refers to components of the finished drug other than the active ingredient such as binding agents (e.g., pregelatinized maize starch, polyvinyl pyrrolidone or hydroxy methyl cellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate).

The term "ionomimetics" as used in the present invention refers to the compounds that may bind to the inorganic ion receptor and mimics the effects of an inorganic ion at an inorganic ion receptor.

The term "ionolytics" as used in the present invention refers to the compounds which bind to an inorganic ion receptor and block one or more activities caused by an inorganic ion at inorganic ion receptor.

The term "calcimimetic" as used in the present invention refers to calcium receptor modulator compound which inhibits the bone re-sorption in vivo by an osteoclast; inhibits bone re-sorption in vitro by an osteoclast; stimulates calcitonin secretion in vitro and in vivo from c-cell; inhibits parathyroid hormone secretion from parathyroid cell in vitro and decreases parathyroid hormone secretion in vivo; elevates calcitonin levels in vivo; or blocks osteoclastic bone re-sorption in vitro and inhibits bone re-sorption in vivo.

The term "subject" as used in the present invention refers to a mammal in which modulation of an inorganic receptor will have a beneficial effect. Subject in need of the treatment involving modulation of inorganic ion receptors can be identified using standard techniques known to those in the medical profession. Preferably, a subject is a human being having a disease or disorder characterized by one or more of the following: (1) abnormal inorganic ion homeostasis, more preferably abnormal calcium homeostasis; (2) an abnormal level of messenger whose production or secretion is affected by calcium receptor activity, more preferably affected by calcium receptor activity; and (3) an abnormal level or activity of a messenger whose function is affected by inorganic ion receptor activity, more preferably affected by calcium receptor activity. Diseases characterized by abnormal calcium receptor homeostasis include hyperparathyroidism, osteoporosis and other bone and mineral related disorders.

The term "therapeutically effective amount" as used in the present invention refers to an amount of an agent which relieves to some extent one or more symptoms of the disease or disorder in the subject; or returns to a normal either partially or completely one or more physiological or biochemical parameters associated with or causative of the disease.

General Instrumental Details

The X-ray diffractograms were obtained using PANalytical diffractometer from X' Pert PRO with vertical goniometer and copper anodic tube, radiations CuKα, $\lambda=1.54$ Å. Thermogravimetric analysis was carried out in vented pant at a scan of 10° C./minute at a temperature range of 30° C. to 300° C. under nitrogen purge using Q 500 available from TA instruments. Differential scanning calorimetry analysis was done using a Mettler Toledo (Model $821^e$).

General Details of HPLC Method
  Column: Octadecylsilane (ODS)
  Dimensions of column: (150×4.6) mm, 5 μm
  Detector: UV at 223 nm
  Mobile phase: Gradient of Buffer: Acetonitrile
  Diluent: 50% Aqueous solution of Acetonitrile
  Stop time: 45 minutes
  Buffer solution: Phosphate buffer pH 6.0

Having thus described the invention with the reference to the particular embodiment and illustrative examples, those skilled in art can appreciate the modifications to the invention as described and illustrated that do not depart from the spirit and the scope of the invention as disclosed in the specifications.

Non-limiting examples of the present invention are as follows.

All the experiments have been carried under an inert atmosphere.

EXAMPLES

Example 1

3-chloro-N-[(1R)-1-(naphthalen-1-yl)ethyl]prop-2-en-1-amine (Formula IV)

Method A:

Potassium carbonate (161.2 g) and potassium iodide (5 g) were added to the mixture of 1,3-dichloropropene (97.3 g) and (R)-1-(1-naphthyl)ethylamine (100 g) in isopropyl alcohol (500 mL) at room temperature. The reaction mixture was refluxed at 80° C. to 85° C. for about 4 hours. After the completion of the reaction, mixture was cooled to room temperature and filtered through hyflo bed. Hyflo bed was washed with isopropyl alcohol (500 mL). The filtrate was combined and treated with hydrochloric acid (6 Normal; 100 mL) at room temperature. The solution was allowed to stir for about one hour at room temperature to give solid. The solid was filtered and was washed twice with isopropyl alcohol (2×100 mL). Methanol (750 mL) was added to the wet solid and stirred for 10-15 minutes at room temperature. The pH of solution was adjusted to 11 to 12 using a solution of sodium hydroxide in water (20%). The solution was diluted with de-ionized water (750 mL) and extracted with dichloromethane (500 mL). Layers were separated and the organic layer was washed twice with de-ionized water (2×500 mL). The organic layer was completely concentrated under vacuum at 40° C. to 45° C. to give 3-chloro-N-[(1R)-1-(naphthalen-1-yl)ethyl]prop-2-en-1-amine as oil.

Weight=74 g
Yield (%)=51.7
$^1$HNMR (δ ppm, CDCl$_3$): 8.12-8.14 (1H, Ar), 7.81-7.83 (1H, Ar), 7.69-7.71 (1H, Ar), 7.58-7.60 (1H, Ar), 7.41-7.49 (3H, Ar), 5.94-6.03 (2H, —CH=CH), 4.57-4.62 (1H, CH—CH$_3$), 3.05-3.16 (2H, CH$_2$—NH$_2$), 1.42-1.52 (3H, CH$_3$).
MS (m/e): 246

Method B:
Potassium carbonate (72.5 g), Tetrabutyl ammonium bromide (30 g) and de-ionized water (75 mL) were added to (R)-1-(1-naphthyl)ethylamine (150 g) in toluene (750 mL) at room temperature. The reaction mixture was heated to 60° C. to 70° C. and added trans 1,3-dichloropropene (126.4 g). The reaction mass was refluxed for 3 hours at 90° C. to 95° C. The reaction mixture was cooled to 40° C., and washed with de-ionized water (2×450 mL). The organic layer was separated and concentrated under vacuum at 55° C. to 60° C. to give an oily residue. The residue was dissolved in acetone (750 mL), added de-ionized water (150 ml) and the pH of the reaction mixture was adjusted to 1-2 using aqueous hydrochloric acid (6 Normal; 150 mL). The solid was stirred at 30° C. to 40° C. for 30 min, cooled to 20° C. to 25° C. and stirred for 1 hour. The resulting solid was filtered and suspended in acetone (300 mL), the suspensions were filtered and washed with acetone (150 mL). The resulting solid was suspended in de-ionized water (300 mL), filtered and washed with de-ionized water (225 mL). The resulting wet solid was suspended in a mixture of toluene (750 mL), methanol (375 mL) and de-ionized water (375 mL). The pH of the mixture was adjusted to 11-11.5 using aqueous sodium hydroxide solution (20%; 150 mL) and stirred for 30 minutes. The layers were separated and organic layer was washed with de-ionized water (2×300 mL). The organic layer was concentrated under reduced pressure to give 3-chloro-N-[(1R)-1-(naphthalen-1-yl)ethyl]prop-2-en-1-amine as an oil.

Weight=165 g

Example 2

3-chloro-N-[(1R)-1-(naphthalen-1-yl)ethyl]prop-2-en-1-amine hydrochloride

Potassium carbonate (161.2 g) and potassium iodide (5 g) were added to a solution of (R)-1(1-naphthyl)ethylamine (100 g) and 1,3-dichloropropene (97.3 g) in acetonitrile (1 L) at room temperature. The reaction mixture was refluxed at 80° C. to 85° C. for 4 hours. After the completion of the reaction, the mixture was cooled to room temperature and de-ionized water (500 mL) was added. The solution was stirred for 15 minutes and layers were separated. The organic layer was concentrated under vacuum at 55° C. to 60° C. till about 100 to 150 mL of residue was left. Toluene (500 mL) was added to the residue and the organic layer was washed twice with de-ionized water (2×250 mL). The organic layer was concentrated under vacuum at 55° C. to 60° C. Isopropyl alcohol was added to the residue and stirred for 10 minutes at room temperature. The pH of the solution was adjusted to 0.5 to 1.0 using concentrated hydrochloric acid (35 mL) and stirred for one hour at room temperature. The solid was filtered, washed with isopropyl alcohol (2×100 mL) and dried under vacuum at 45° C. to 50° C.

Dry Weight=80.0 g
Yield (%)=48.5

Example 3

3-(trifluoromethyl)phenyl]magnesium bromide (Formula V)

Method A:
A solution of 3-trifluoromethylbromobenzene (77.9 g) and 1,2-dibromoethane (6.9 mL) in tetrahydrofuran (250 mL) was added to a mixture of activated magnesium (18.4 g) in tetrahydrofuran (150 mL) under inert atmosphere. The reaction mixture was refluxed at 60° C. to 65° C. for about 2 hours, filtered and stored under inert atmosphere at 5° C. to 10° C. for further use.

Method B:
A solution of 3-trifluoromethylbromobenzene (151.1 g) in tetrahydrofuran (200 mL) was added to a mixture of activated magnesium (38.4 g) in tetrahydrofuran (300 mL) under inert atmosphere at reflux temperature (60° C. to 65° C.) in 1 hour. The reaction mixture was refluxed for about 1 hour. The reaction mixture was cooled to −45° C. to −40° C. and carried over to the next step.

Example 4

1-[3-(trifluoromethyl)phenyl]prop-2-en-1-ol (Formula VII)

3-(Trifluoromethyl)benzaldehyde (100 g) was added to a pre-cooled (0 to 5° C.) solution of vinyl magnesium bromide (862 mL; 1M) in tetrahydrofuran under the nitrogen atmosphere. The reaction mixture was stirred at room-temperature for one hour. After completion, the reaction was quenched with de-ionized water (500 mL) and dichloromethane (500 mL) was added. The dichloromethane layer was washed with sodium bicarbonate solution (7%; 500 mL), layers were separated and organic layer was concentrated under vacuum at 40° C. to 45° C. to give 1-[3-(trifluoromethyl)phenyl]prop-2-en-1-ol as oil.

Dry Weight=110 g
% Yield=94.8

Example 5

3-[3-(trifluoromethyl)phenyl]prop-2-en-1-ol (Formula VIII)

Methanesulphonic acid (59.4 g) was added to a solution of 1-[3-(trifluoromethyl)phenyl]prop-2-en-1-ol (50 g) in tetrahydrofuran (200 mL) and de-ionized water (100 mL) at room temperature. Reaction mixture was refluxed at 65° C. to 70° C. for about 20-22 hours. After completion of the reaction, de-ionized water (50 mL) and toluene (200 mL) were added to organic layer. Organic layer was separated and neutralized to pH 7.5-8.0 using solution of sodium bicarbonate (7%), and concentrated under vacuum to give 3-[3-(trifluoromethyl)phenyl]prop-2-en-1-ol as oil.

Dry Weight=48.5 g
% Yield=97

Example 6

1-[3-chloroprop-1-en-1-yl]-3-(trifluoromethyl)benzene (Formula X)

Dimethylformamide (5 mL) was added to a solution of 3-[3-(trifluoromethyl)phenyl]prop-2-en-1-ol (50 g) in dichloromethane (500 mL) at 0 to 5° C. Thionyl chloride (44.2 g) was slowly added to the above mixture maintaining the temperature at about 0 to 5° C. The reaction mixture was stirred at 0 to 5° C. for 1-2 hours. After completion of the reaction, the mixture was quenched with ice-chilled de-ionized water (250 mL) at 0-10° C. and stirred for 30 minutes. Organic layer was separated, washed twice with a solution of sodium chloride (10%; 250 mL) and concentrated under vacuum to give 1-[3-chloroprop-1-en-1-yl]-3-(trifluoromethyl)benzene.

Dry Weight=51.9 g
% Yield=95.3

Example 7

1-(1-chloroprop-2-en-1-yl)-3-(trifluoromethyl)benzene (Formula IX)

Dimethylformamide (5 mL) was added to a solution of 1-[3-(trifluoromethyl)phenyl]prop-2-en-1-ol (50 g) in dichloromethane (500 mL) at 0 to 5° C. The reaction mixture was stirred for 5-10 min at room temperature. The reaction mixture was cooled at 0 to 5° C. and thionyl chloride (44.26 g) was added slowly maintaining the temperature at 0 to 5° C. The reaction mixture was stirred at 0 to 5° C. for 1-2 hours. After completion of the reaction, the mixture was quenched slowly with ice-chilled de-ionized water (250 mL) at 0-10° C. and stirred for additional 30 minutes at 0 to 5° C. Organic Layer was separated, washed twice with a solution of sodium chloride (10%; 250 mL) and concentrated under vacuum at 40° C. to 45° C. to give 1-(1-chloroprop-2-en-1-yl)-3-(trifluoromethyl)benzene.

Dry Weight=52 g
% Yield=95.5

Example 8

N-[(1R)-1-(naphthalen-1-yl)ethyl]-3-[3-(trifluoromethyl)phenyl]prop-2-en-1-amine hydrochloride Method A:
A solution of 3-chloro-N-[(1R)-1-(naphthalen-1-yl)ethyl]prop-2-en-1-amine (Example 1; 50 g), iron acetylacetonate (3.6 g) and N-methyl-2-pyrrolidone (1.0 g) in tetrahydrofuran (200 mL) at 0 to −5° C. was added to a solution of 3-(trifluoromethyl)phenyl magnesium bromide (Example 3) in tetrahydrofuran (150 mL) at −25° C. to −30° C. under inert atmosphere. The reaction mixture was stirred at 0 to 5° C. for 15 to 20 minutes. After the completion of the reaction, de-ionized water (75 mL) was added at 0 to 10° C. Toluene (250 mL) was added to the reaction mixture and the pH of mixture was adjusted to 0 to 1 using hydrochloric acid (6 Normal; 250 mL) at 10° C. to 35° C. and stirred at the same temperature for about 15 minutes. Layers were separated, and the organic layer was washed with de-ionized water (2×250 mL) and concentrated under vacuum at 55° C. to 60° C. Isopropyl alcohol (125 mL) was added to the residue obtained and heated to 40° C. to 45° C. to get a clear solution. The solution was cooled to 20° C. to 30° C. and stirred for about 2 hours to give solid. The solid was filtered, washed with isopropyl alcohol (2×50 mL) and dried under vacuum at 45° C. to 50° C. to give N-[(1R)-1-(naphthalen-1-yl)ethyl]-3-[3-(trifluoromethyl)phenyl]prop-2-en-1-amine hydrochloride.

Dry Weight=56.0 g
Yield (%)=70.23

Alternatively, 3-chloro-N-[(1R)-1-(naphthalen-1-yl)ethyl]prop-2-en-1-amine used in Example 8 can be prepared by following method:

The pH of the solution of 3-chloro-N-[(1R)-1-(naphthalen-1-yl)ethyl]prop-2-en-1-amine hydrochloride (50 g) in methanol (500 mL) was adjusted to 11 to 12 using aqueous sodium hydroxide solution (~20% w/v) at room temperature. De-ionized water (500 ml) was added to the solution. The mixture was extracted with dichloromethane (250 mL). Layers were separated and the aqueous layer was re-extracted with dichloromethane (125 mL). The combined organic layers were washed with de-ionized water (2×250 mL) and concentrated under vacuum at 35° C. to 40° C. to give 3-chloro-N-[(1R)-1-(naphthalen-1-yl)ethyl]prop-2-en-1-amine as oil.

Weight: 43 g
Yield (%): 98.8

Method B:
Anhydrous potassium carbonate (64.0 g) and (R)-1-(1-naphthyl)ethylamine (39.0 g) was added to a solution of 1-[3-chloroprop-1-en-1-yl]-3-(trifluoromethyl)benzene (Example 6; 50 g) in acetonitrile (500 mL) at room temperature. The reaction mixture was refluxed for 12 hours at 80° C. to 85° C. After completion of the reaction, the mixture was quenched with de-ionized water (250 mL). The organic layer was separated and completely distilled off to remove acetonitrile to obtain oil. The oil obtained was dissolved in toluene (500 mL) and added to de-ionized water (250 mL). The pH of this mixture was adjusted to 0.1-0.5 by adding solution of hydrochloric acid (6 N; 100 mL). The mixture was stirred at 50° C. to 60° C. for 15-20 minutes, followed by the layer separation. The organic layer was acidified with hydrochloric acid (6N; 50 mL) and stirred at 50° C. to 60° C. for 15-20 minutes. The organic layer was completely distilled off to obtain N-[(1R)-1-(naphthalen-1-yl)ethyl]-3-[3-(trifluoromethyl)phenyl]prop-2-en-1-amine hydrochloride.

Dry Weight=77.0 g
% Yield=86.03

Method C:
N-[(1R)-1-(naphthalen-1-yl)ethyl]-3-[3-(trifluoromethyl)phenyl]prop-2-en-1-amine hydrochloride was also prepared by using 1-(1-chloroprop-2-en-1-yl)-3-(trifluoromethyl)benzene (Example 7; 50 g) in place of 1-[3-chloroprop-1-en-1-yl]-3-(trifluoromethyl)benzene.

Dry Weight=80 gm
% Yield=89%

$^1$HNMR (δ ppm, CDCl$_3$) 1.97 (3H, C$\underline{H}_3$), 3.55 (2H, CH$_2$—NH—), 5.26 (1H, —C$\underline{H}$—CH$_3$), 6.14 (1H, Ar—C$\underline{H}$=CH), 6.52 (1H, Ar—CH=C$\underline{H}$), 7.27-8.31 (11H, Ar—$\underline{H}$), 10.6 (2H, —N$\underline{H}_2^+$)

MS (m/e) 355

Example 9

Recrystallization of N-[(1R)-1-(naphthalen-1-yl)ethyl]-3-[3-(trifluoromethyl)phenyl]prop-2-en-1-amine hydrochloride A solution of N-[(1R)-1-(naphthalen-1-yl)ethyl]-3-[3-(trifluoromethyl)phenyl]prop-2-en-1-amine hydrochloride (15.6 g) in methyl tertiary butyl ether (160 mL) is stirred at 40° C. to 45° C. for 1 hour. The solution was slowly cooled to room temperature in 30 minutes and stirred at the same temperature for 90 minutes. The solid was filtered and washed with methyl tertiary butyl ether (30 mL). The product obtained was dried under vacuum at 40° C. to 45° C.

Weight=6.1 g

Hexane (160 mL) was added to a clear solution of N-[(1R)-1-(naphthalen-1-yl)ethyl]-3-[3-(trifluoromethyl)phenyl]prop-2-en-1-amine hydrochloride (15.6 g) in toluene (63 mL) at 40° C. to 45° C. and stirred for 1 hour. The solution was slowly cooled to room temperature in 30 minutes and stirred at the same temperature for 90 minutes. The solid was filtered and washed with mixture of toluene and hexane (1:4; 25 mL). The product obtained was washed with methyl-tertiary butyl ether (15 ml) was dried under vacuum at 45° C. to 50° C.

Weight=6.7 g

Hexane (95 mL) was added to a clear solution of N-[(1R)-1-(naphthalen-1-yl)ethyl]-3-[3-(trifluoromethyl)phenyl]prop-2-en-1-amine hydrochloride (15.6 g) in ethyl acetate (31 mL) at 40° C. to 45° C. and stirred for 1 hour. The solution was slowly cooled to room temperature in 30 minutes and stirred at the same temperature for 90 minutes. The solid was filtered and washed with mixture of ethyl acetate and hexane (1:4; 25 mL). The product obtained was dried under vacuum at 45° C. to 50° C.

Weight=6.2 g

A solution of N-[(1R)-1-(naphthalen-1-yl)ethyl]-3-[3-(trifluoromethyl)phenyl]prop-2-en-1-amine hydrochloride (15.6 g) in di-isopropyl ether (95 mL) is stirred at 35° C. to 40° C. for 1 hour. The solution was slowly cooled to room temperature in 30 minutes and stirred at the same temperature for 90 minutes. The solid was filtered and washed with diisopropyl ether (30 mL). The product obtained was dried under vacuum at 45° C. to 50° C.

Weight=7.7 g

Hexane (125 mL) was added slowly to a solution of N-[(1R)-1-(naphthalen-1-yl)ethyl]-3-[3-(trifluoromethyl)phenyl]prop-2-en-1-amine hydrochloride (15.6 g) in isopropyl alcohol (32 mL) and stirred for 2 hours at room temperature. The solid was filtered and washed with mixture of isopropyl alcohol and hexane (2:8 v/v; 30 mL). The product obtained was dried under vacuum at 45° C. to 50° C.

Weight=5.2 g

Example 10

N-[(1R)-1-(naphthalen-1-yl)ethyl]-3-[3-(trifluoromethyl)phenyl]prop-2-en-1-amine hydrobromide A solution of 3-chloro-N-[(1R)-1-(naphthalen-1-yl)ethyl]prop-2-en-1-amine (Example 1 or 3; 110 g), iron acetylacetonate (3.6 g) and N-methyl-2-pyrrolidone (1.0 g) in tetrahydrofuran (300 mL) at 0 to –5° C. was added to a solution of 3-(trifluoromethyl)phenyl magnesium bromide (Example 4) in tetrahydrofuran (500 mL) at –45° C. to –40° C. under inert atmosphere. The reaction mixture was stirred at 0 to –5° C. for 10 minutes. After the completion of the reaction, de-ionized water (150 mL) was added at 0 to 25° C. Aqueous hydrochloric acid (6 N; 500 mL) was added at 25° C. to 35° C. and the mixture was stirred for 1 hour. Toluene (500 mL) was charged to the mixture and stirred for 10 minutes. Layers separated and the organic layer was washed with aqueous solution of hydrochloric acid (0.5N; 2×500 mL). pH of the organic layer was adjusted to about 8.5 using aqueous sodium hydroxide (10%). Layers were separated, and the organic layer was washed with de-ionized water (2×250 mL) and concentrated under vacuum at 55° C. to 60° C. to give an oily residue (180 g).

The residue (90 g) was dissolved in isopropyl alcohol (200 mL). Aqueous hydrobromic acid (47%; 55.4 g) was added at 20° C. to 25° C. to the resulting solution and mixture was stirred at same temperature for 30 minutes and finally cooled to 0-5° C. and stirred at this temperature for about one hour. The resulting suspensions were filtered and washed with pre-cooled isopropyl alcohol (0-5° C.; 50 mL). The solid obtained was suspended in isopropyl acetate (100 mL), filtered and washed with isopropyl acetate (50 mL). The resulting solid was dried under vacuum at 50° C. to 55° C. to give N-[(1R)-1-(naphthalen-1-yl)ethyl]-3-[3-(trifluoromethyl)phenyl]prop-2-en-1-amine hydrobromide.

Dry Weight=47.5 g

Example 11

N-[(1R)-1-(naphthalen-1-yl)ethyl]-3-[3-(trifluoromethyl)phenyl]prop-2-en-1-amine fumarate Aqueous solution of sodium bicarbonate (5% in water; 30 mL) was added to a solution of N-[(1R)-1-(naphthalen-1-yl)ethyl]-3-[3-(trifluoromethyl)phenyl]prop-2-en-1-amine hydrochloride (5.0 g) in ethyl acetate (30 mL) at room temperature and stirred for 1 hour. After completion of the reaction, product was extracted with ethyl acetate (50 mL). The organic layer was washed with water (30 mL), passed through hyflo bed and hyflo bed was washed with ethyl acetate (10 mL). The ethyl acetate layer was concentrated to about 30 mL. Fumaric acid (2 g) was added to the concentrated ethyl acetate layer at room temperature and stirred for about one hour to obtain the precipitates of N-[(1R)-1-(naphthalen-1-yl)ethyl]-3-[3-(trifluoromethyl)phenyl]prop-2-en-1-amine fumarate. The solid was filtered, washed with ethyl acetate twice (2×10 mL) and dried under vacuum.

Weight=4.9 g

Yield (%)=81.4

$^1$HNMR (δ ppm DMSO-$d_6$): 1.50 (CH$_3$), 3.40 (2H, CH$_2$—NH—), 4.90 (1H, —CH—CH$_3$), 6.46-6.62 (Ph CH=CH and CH=CH fumaric acid), 7.51-8.24 (11H, aromatic)

Example 12

N-[(1R)-1-(naphthalen-1-yl)ethyl]-3-[3-(trifluoromethyl)phenyl]prop-2-en-1-amine citrate Aqueous solution of sodium bicarbonate (5% in water; 30 mL) was added to a solution of N-[(1R)-1-(naphthalen-1-yl)ethyl]-3-[3-(trifluoromethyl)phenyl]prop-2-en-1-amine hydrochloride (5.0 g) in ethyl acetate (25 mL) at room temperature and stirred for about 30 minutes. After completion of the reaction, the organic layer was washed with water (30 mL). The ethyl acetate layer was concentrated under vacuum. Absolute alcohol (25 mL) was added to the concentrated residue and stirred for about 10 minutes at room temperature. Citric acid (2.46 g) was added to the solution of the residue in alcohol and refluxed till citric acid was completely dissolved. The resultant solution was cooled to 40° C. to 45° C. and passed through hyflo bed. The hyflo bed was washed with absolute alcohol (25 mL). Organic layer was concentrated under vacuum at below 60° C. Ethyl acetate (25 mL) was added to the concentrated organic layer and the mixture was heated at 40° C. to 45° C. for about 1 hour. The reaction mixture was allowed to cool to room temperature and stirred for one hour at room temperature to obtain solid. The solid was filtered, washed with ethyl acetate (5 mL) and dried under vacuum.

Weight=4.2 g
Yield (%)=60.1
$^1$HNMR (δ ppm, DMSO-$d_6$) 1.61 (3H, C$\underline{H}_3$), 2.5 (4H, citric acid), 3.6 (2H, NH—C$\underline{H}_2$), 5.1 (1H, CH$_3$—C$\underline{H}$), 6.4-6.7 (CH═CH), 7.5-8.3 (11H, Ar—H)

Example 13

Preparation of Cinacalcet

Method A:
To a solution of N-[(1R)-1-(naphthalen-1-yl)ethyl]-3-[3-(trifluoromethyl)phenyl]prop-2-en-1-amine Hydrochloride (Example 8; 75 g) in methanol (750 mL) was added 10% palladium on carbon (24 g). The reaction mixture was stirred at room temperature under an atmosphere of hydrogen gas (5 Kg pressure) for 2-3 hours. After completion of the reaction, the catalyst was filtered and washed with methanol. Methanol was completely distilled off under vacuum to obtain oil. The oil obtained was treated in methyl tertiary butyl ether (500 mL) and stirred at 35° C. to 40° C. for 1-2 hours to precipitate the product. The product was filtered, washed with methyl tertiary butylether (100 mL) and dried under vacuum at room-temperature for 10-12 hours.

Dry Weight=38 g
% Yield=50.4

Method B:
Aqueous sodium hydroxide (10%; 22 mL) was added to a solution of N-[(1R)-1-(naphthalen-1-yl)ethyl]-3-[3-(trifluoromethyl)phenyl]prop-2-en-1-amine hydrobromide (Example 5; 23 g) in toluene (125 mL) and de-ionized water (50 mL) to adjust to pH to 8-8.5. The resulting mixture was stirred for 10 minutes at room temperature. Layers were separated and organic layer was washed with de-ionized water (75 mL). The organic layer was concentrated under vacuum at 50° C. to 60° C. to give a residue. The resulting residue was dissolved in ethyl acetate (125 mL) and palladium/carbon catalyst (2.5% w/w, 50% wet, 9.2 g) was added to it at room temperature. The reaction mixture was stirred under an atmosphere of hydrogen gas (4-5 Kg pressure) at 25° C. to 35° C. for 2 hours. After completion of the reaction, the catalyst was filtered and washed with ethyl acetate (115 mL). The combined filtrate was washed with aqueous hydrochloric acid (1 Normal; 75 mL) and further washed with de-ionized water (50 mL). Activated carbon (0.5 g) was added to the organic layer and stirred for 20-30 minutes at room temperature. The carbon treated layer was filtered through hyflo bed and washed with ethyl acetate (50 mL). The filtrate was further passed through 0.45 micron filter paper. The resulting filtrate was concentrated under vacuum at 55° C. to 60° C. to give a residue. Ethyl acetate (150 mL) was added to the residue, heated to get a clear solution and concentrated to 75 mL under vacuum at 55° C. to 60° C. Ethyl acetate (230 mL) was again added to the resulting residue, heated to 65° C. to 70° C. to get a clear solution and concentrated under vacuum at 55° C. to 60° C. (till about 115 mL is left). The resulting mixture was allowed to cool to 50° C. and further cooled to 20° C. to 30° C. and stirred at the same temperature for about 1 hour. The mixture was finally cooled 0 to −5° C. and stirred at same temperature for 1 hour. The resulting solid was filtered. The solid obtained was suspended in pre-cooled ethyl acetate (0 to 5° C.; 50 mL) and filtered. The product obtained was further washed with ethyl acetate (25 mL) and dried under vacuum at 50° C. to 55° C. for about 15 hours.

Dry Weight=13 g
HPLC purity (%): 99.92

Method C:
Ethyl acetate (23 mL) and de-ionized water (11.5 mL) was added to a mixture of N-[(1R)-1-(naphthalen-1-yl)ethyl]-3-[3-(trifluoromethyl)phenyl]prop-2-en-1-amine hydrobromide (Example 11; 23 g) and ethyl acetate (115 mL) and stirred to get a clear solution. Palladium/carbon (2.5% w/w; 50% wet, 9.2 g) was added to the resulting solution. The reaction mixture was stirred under hydrogen atmosphere (4-5 Kg pressure) for 2 hours at 25° C. to 35° C. After the completion of the reaction, mixture was filtered through hyflo bed and washed with ethyl acetate (115 mL). De-ionized water (70 mL) was added to the filtrate. The pH of the mixture was adjusted to 8.4-8.6 using aqueous sodium hydroxide solution (20%; 21 mL) and the mixture was stirred for 10 minutes at room temperature. Layers were separated and organic layer was washed with de-ionized water (70 mL). The organic layer was washed with aqueous hydrochloric acid (1 Normal; 75 mL) and resulting mixture was stirred for 10 minutes at room temperature. The organic layer was again washed with de-ionized water (50 mL) and concentrated under vacuum at 55° C. to 60° C. to a residue. Ethyl acetate (150 mL) was added to the residue, heated to dissolve and recovered (75 mL) at 55° C. to 60° C. Ethyl acetate (230 mL) was again added to the resulting residue and heated to 65° C. to 70° C. to get a clear solution. The resulting solution was concentrated under vacuum at 55° C. to 60° C. (till about 115 mL residue is left). The resulting residue was allowed to cool to 50° C. to 55° C. and further cooled 20° C. to 30° C. and stirred at the same temperature for about 1 hour. The mixture was finally cooled 0 to −5° C. and stirred at same temperature for 1 hour. The resulting solid was filtered. The solid obtained was suspended in pre-cooled ethyl acetate (0-5° C.; 50 mL) and filtered. The product obtained was further washed with ethyl acetate (25 mL) and dried under vacuum at 50° C. to 55° C. for about 15 hours.

Dry Weight=15 g
HPLC purity (%): 99.87
Compound of Formula VI (unsaturated cinacalcet): not detectable (LOD is 0.02%)
Any unknown impurity (%): 0.06
Total impurities (%): 0.13

Method D:
Vitride® solution (70% w/w in toluene, 79.5 g) was added to a suspension of N-[(1R)-1-(naphthalen-1-yl)ethyl]-3-[3-(trifluoromethyl)phenyl]prop-2-en-1-amine hydrobromide (Example 11; 30 g) in toluene (150 ml) at 25° C. to 35° C. under inert atmosphere. The reaction mixture was heated at 60° C. to 70° C. for 1.5 hours. After completion of reaction, the mixture was cooled to 10° C. to 15° C. and added to pre-cooled (5 to 10° C.) aqueous sodium hydroxide solution (10%; 150 ml). The mixture was stirred for 30 minutes at 25° C. to 35° C., layers were settled and separated. The organic layer was washed with de-ionized water (2×60 ml), hydrochloric acid (6 Normal; 17 ml), de-ionized water (2×60 ml) and concentrated under vacuum. Ethyl acetate (360 ml) was added to the residue and heated to 60° C. to 70° C. The resulting solution was concentrated under vacuum (till 210 ml of solvent was recovered). The resulting slurry was allowed to cool to room temperature and finally cooled at 0 to 5° C. for 1 hour. The solid was filtered, washed with pre-cooled ethyl acetate (5° C. to 10° C.; 2×30 ml) and dried at 50° C. to 55° C. for 10 hours.

Dry wt=10.5 g

Method E:
Palladium catalyst (2 g; 2-5% w/w on carbon) and concentrated hydrochloric acid (8.85 mL) was added to a solution of N-[(1R)-1-(naphthalen-1-yl)ethyl]-3-[3-(trifluoromethyl)phenyl]prop-2-en-1-amine fumarate (Example 11; 10 g) in methanol (100 ml) at room temperature under hydrogen gas pressure (4-5 kg) and stirred for 2-3 hours at 25° C. to 30° C. After completion of the reaction, reaction mixture was filtered through hyflo bed and methanol was recovered under vacuum at 50° C. to 55° C. to obtain a residue. Toluene (50 mL) and de-ionized water (50 mL) was added to the residue and stirred for about 10 minutes at 50° C. to 55° C. Layers were separated and the aqueous layer was extracted with toluene (50 mL). The combined toluene layer was washed with water (50 mL) and recovered under vacuum at a temperature below 60° C. Methyl tertiary butyl ether (100 mL) was added to the concentrated residue and stirred for about 1 hour to obtain slurry. Solid was filtered, washed and dried under vacuum at 45° C. to 50° C.

Weight=7 g
Yield (%)=83.8%

Method F:

N-[1-(R)-(−)-(1-naphthyl)ethyl]-3-[3-(trifluoromethyl)phenyl]-1-aminopropane hydrochloride (cinacalcet) can be prepared starting from N-[(1R)-1-(naphthalen-1-yl)ethyl]-3-[3-(trifluoromethyl)phenyl]prop-2-en-1-amine citrate (Example 12; 10 g);

Weight=5 g
Yield (%)=69.5

Method G:

Palladium catalyst (2.0 g; 2.5% w/w on carbon) was added to a solution of N-[(1R)-1-(naphthalen-1-yl)ethyl]-3-[3-(trifluoromethyl)phenyl]prop-2-en-1-amine citrate (Example 12; 10 g) in methanol (100 mL) under hydrogen pressure (4-5 kg). After the completion of reaction, the reaction mixture was filtered through hyflo bed and washed with methanol (50 mL). The filtrate was concentrated under vacuum to give foam like material. The foam like material was dissolved in ethyl acetate (25 mL) and concentrated to get a gummy residue (9.6 g).

To the solution of the gummy residue (8.0 g) in methanol (40 mL) was added hydrochloric acid (conc. 6.1 mL) and stirred for 1 hour at 25° C. to 30° C. The reaction mixture was completely concentrated under vacuum at 50° C. to 55° C. Toluene (40 mL) and de-ionized water (40 ml) was added and the resultant mixture was stirred for 10 minutes at room temperature. The aqueous layer was extracted with toluene (40 ml). The combined organic layer was washed with de-ionized water and concentrated under vacuum at 50° C. to 55° C. The residue obtained was dissolved in methyl tertiary butyl ether (80 mL) and heated at 40° C. to 45° C. for 10-15 minutes. The mixture was allowed to stir for another one hour at 40° C. to 45° C., cooled to 25° C. to 30° C. in 30 minutes and further stirred at 25° C. to 30° C. for 1 hour. The solid was filtered, washed with methyl tertiary butyl ether (2×15 mL) and dried under vacuum at 45° C. to 50° C.

Weight=4.6 g
Yield (%)=63.9

Method H:

To a solution of N-[(1R)-1-(naphthalen-1-yl)ethyl]-3-[3-(trifluoromethyl)phenyl]prop-2-en-1-amine hydrochloride (Example 8; 15 g) in methanol (15 mL) and ethyl acetate (75 ml) was added Raney nickel (15 g). The reaction mixture was stirred at room temperature under an atmosphere of hydrogen gas (5 Kg pressure) for 1 to 5 hours. After completion of the reaction, the catalyst was filtered and washed with ethyl acetate (3×15 mL). The combined filtrate was concentrated under vacuum to give a residue. Ethyl acetate (210 mL) was added to the residue and refluxed to get a clear solution. Ethyl acetate was recovered under vacuum (~125 mL) and the solution was cooled to 25° C. to 30° C. in about 30 minutes. The solid obtained was filtered, washed with ethyl acetate (15 mL) and dried under vacuum at 45° C. to 50° C. for about 15 hours.

Dry Weight=10.5 g
Yield (%)=69.6

Example 14

Purification of Cinacalcet (Pure)

Crude cinacalcet (38 g) was added to methyl tertiary butyl ether (250 mL) to obtain slurry. The slurry was stirred at 45° C. to 50° C. for 1 hour, cooled to 25° C. to 30° C. in 30 minutes and stirred for additional 1 hour at 25° C. to 30° C. The solid obtained was filtered, washed with methyl tertiary butyl ether (100 mL) and finally dried under vacuum at room temperature.

Dry Weight=36 g
% Yield=94.73

$^1$HNMR (δ ppm, CDCl$_3$) 1.97 (3H, C$\underline{H}_3$), 2.28 (2H, —CH$_2$—C$\underline{H}_2$—), 2.51 (2H, —CH$_2$—C$\underline{H}_2$—), 2.54 (2H, C$\underline{H}_2$—NH—), 5.21 (1H, —C$\underline{H}$—CH$_3$), 7.27-8.31 (11H, Ar—$\underline{H}$), 10.4 (2H, —NH$_2^+$).

MS (m/e): 357

We claim:

1. A process for preparing cinacalcet base of Formula I

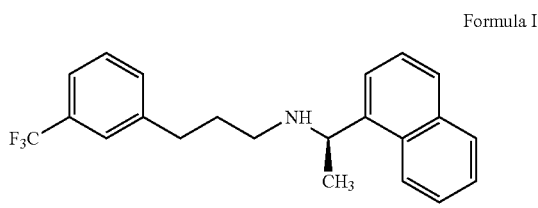 [SMILES: C[C@@H](NCCCc1cccc(C(F)(F)F)c1)c1cccc2ccccc12]

Formula I or a pharmaceutically acceptable salt thereof comprising the steps of:

a) reacting 1,3-dichloropropene of Formula II with (R)-1-(1-naphthyl)ethylamine of Formula III

Formula II

Formula III to give a compound of Formula IV; and

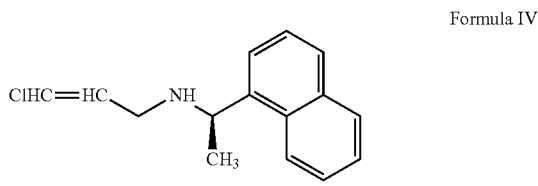

Formula IV b) converting the compound of Formula IV or its salts to cinacalcet base or pharmaceutically acceptable salts thereof.

2. A process for preparing cinacalcet base of Formula I and its pharmaceutically acceptable salts, comprising the steps of a) reacting a compound of Formula IV with 3-trifluoromethyl phenyl metal halide of Formula V

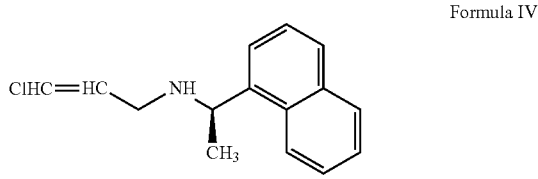

Formula IV

-continued

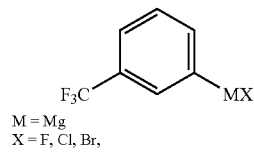

M = Mg
X = F, Cl, Br, to give a compound of Formula VI; and

Formula VI

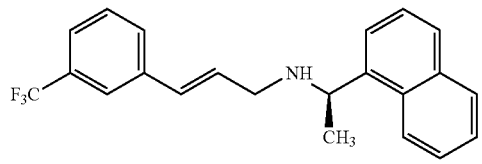

b) reducing the compound of Formula VI or salts thereof to obtain cinacalcet as the base or a salt.

3. The process according to claim 2, wherein the 3-trifluoromethyl phenyl metal halide is selected from a group consisting of 3-trifluoromethyl phenyl magnesium chloride and 3-trifluoromethyl phenyl magnesium bromide.

4. The process of claim 1, further comprising the steps of
c) reacting a compound of Formula IV with 3-trifluoromethyl phenyl metal halide of Formula V Formula IV

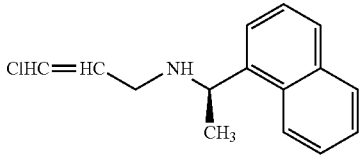

Formula V

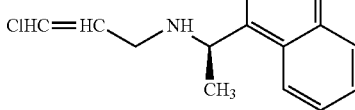

M = Mg
X = F, Cl, Br, to give a compound of Formula VI; and
d) reducing the compound of Formula VI or salts thereof to obtain cinacalcet as the base or a salt.

* * * * *

UNITED STATES PATENT AND TRADEMARK OFFICE
CERTIFICATE OF CORRECTION

PATENT NO. : 8,759,586 B2
APPLICATION NO. : 13/496834
DATED : June 24, 2014
INVENTOR(S) : Sayeed Mukhtar et al.

It is certified that error appears in the above-identified patent and that said Letters Patent is hereby corrected as shown below:

In the Drawings

DRAWING SHEET 11 of 14: "Table 1: Peak table for Figure 1 (Hydrochloride salt of N-[(1R)-1-(naphthalen-1-yl)ethyl]-3-[3-(trifluomethyl)phenyl]prop-2-en-1-amine)" should read -- Table 1: Peak table for Figure 1 (Hydrochloride salt of N-[(1R)-1-(naphthalen-1-yl)ethyl]-3-[3-(trifluoromethyl)phenyl]prop-2-en-1-amine) --

DRAWING SHEET 12 of 14: "Table 2: Peak table for Figure 4 (Hydrobromide salt of N-|(1R)-1-(naphthalen-1-yl)ethyl]-3-[3-(trifluomethyl)phenyl]prop-2-en-1-amine)" should read -- Table 2: Peak table for Figure 4 (Hydrobromide salt of N-[(1R)-1-(naphthalen-1-yl)ethyl]-3-[3-(trifluoromethyl)phenyl]prop-2-en-1-amine) --

DRAWING SHEET 13 of 14: "Table 3: Peak table for Figure 5 (Fumarate salt of N-[(1R)-1-(naphthalen-1-yl)ethyl]-3-[3-(trifluomethyl)phenyl]prop-2-en-1-amine)" should read -- Table 3: Peak table for Figure 5 (Fumarate salt of N-[(1R)-1-(naphthalen-1-yl)ethyl]-3-[3-(trifluoromethyl)phenyl]prop-2-en-1-amine) --

DRAWING SHEET 14 of 14: "Table 4: Peak table for Figure 8 (Citrate salt of N-[(1R)-1-(naphthalen-1-yl)ethyl]-3-[3-(trifluomethyl)phenyl]prop-2-en-1-amine)" should read -- Table 4: Peak table for Figure 8 (Citrate salt of N-[(1R)-1-(naphthalen-1-yl)ethyl]-3-[3-(trifluoromethyl)phenyl]prop-2-en-1-amine) --

Signed and Sealed this
Third Day of February, 2015

Michelle K. Lee
*Deputy Director of the United States Patent and Trademark Office*

CERTIFICATE OF CORRECTION (continued)
U.S. Pat. No. 8,759,586 B2

In the Specification

COLUMN 24, LINES 8-9:
"2.54 (2H, C H$_2$-NH-)," should read -- 2.54 (2H, CH$_2$-NH-) --